(12) United States Patent
Morrow et al.

(10) Patent No.: US 10,946,140 B2
(45) Date of Patent: Mar. 16, 2021

(54) SYSTEMS AND METHODS FOR MEASUREMENT OF FLUID DELIVERY

(71) Applicant: MEDTRONIC MINIMED, INC., Northridge, CA (US)

(72) Inventors: Edward C. Morrow, Irvine, CA (US); Carl A. Link, Westlake Village, CA (US); Adam S. Trock, Simi Valley, CA (US); Andrew E. Weaver, Granada Hills, CA (US); Roshanne Malekmadani, Palo Alto, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 226 days.

(21) Appl. No.: 16/158,223

(22) Filed: Oct. 11, 2018

(65) Prior Publication Data
US 2020/0114075 A1 Apr. 16, 2020

(51) Int. Cl.
*A61M 5/168* (2006.01)
*A61M 5/142* (2006.01)
*A61M 5/172* (2006.01)
*G01F 1/64* (2006.01)

(52) U.S. Cl.
CPC .... *A61M 5/16831* (2013.01); *A61M 5/14248* (2013.01); *A61M 5/172* (2013.01); *A61M 2205/3334* (2013.01); *G01F 1/64* (2013.01)

(58) Field of Classification Search
CPC ........................................................ G01F 1/64
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,058 A * | 9/1999 | Flaherty ............ A61M 5/14276 128/899 |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |

(Continued)

*Primary Examiner* — Paul M. West
*Assistant Examiner* — Mark A Shabman
(74) *Attorney, Agent, or Firm* — Shumaker & Sieffert, P.A.

(57) ABSTRACT

A test system for measuring a volume of fluid dispensed by a fluid infusion device includes a test housing. The test housing includes an inlet and an internal channel. The inlet is to be coupled to the fluid infusion device to receive the volume of fluid, and the internal channel is in fluid communication with the inlet. The test system includes an input electrode coupled to the internal channel to be in fluid communication with the volume of fluid, and an output electrode coupled to the internal channel to be in fluid communication with the volume of fluid. The test system includes a power source configured to create a voltage potential between the input electrode and the output electrode. The volume of fluid in the internal channel conducts current between the input electrode and the output electrode to facilitate measurement of the volume of fluid dispensed.

20 Claims, 14 Drawing Sheets

(56) References Cited

U.S. PATENT DOCUMENTS

| | | |
|---|---|---|
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |
| 2011/0037325 A1* | 2/2011 | Ciocanel ............... F04F 99/00 310/11 |
| 2014/0207065 A1 | 7/2014 | Yavorsky |
| 2016/0331877 A1 | 11/2016 | Braga et al. |
| 2019/0234903 A1 | 8/2019 | Duarte et al. |

* cited by examiner

SYSTEMS AND METHODS FOR MEASUREMENT OF FLUID DELIVERY

TECHNICAL FIELD

Embodiments of the subject matter described herein relate generally to systems and methods for measuring a fluid delivery by a medical device. More particularly, embodiments of the subject matter relate to systems and methods for electrofluidic measurement of a fluid delivery by a fluid infusion device, such as an insulin infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a set connector of an infusion set, which is coupled to the fluid reservoir.

Delivery accuracy of the fluid infusion device is necessary to ensure that the patient receives the correct amount of insulin. Generally, each fluid infusion device is subjected to testing to ensure that the amount of fluid delivered by the fluid infusion device is accurate. Current test methods rely on a gravimetric balance. Due to the small amount of fluid delivered by the fluid infusion device, the measurement of the fluid delivered using the gravimetric balance may be influenced by external factors, such as temperature of the testing environment, evaporation, vibrations, humidity and air density.

Accordingly, it is desirable to provide systems and methods for measuring a delivery of a fluid by a fluid infusion device, such as an insulin infusion device. Moreover, it is desirable to provide systems and methods for measuring an amount of fluid delivered by a fluid infusion device that is resistant to external factors. Furthermore, other desirable features and characteristics will become apparent from the subsequent detailed description and the appended claims, taken in conjunction with the accompanying drawings and the foregoing technical field and background.

BRIEF SUMMARY

In various embodiments, a test system for measuring a volume of fluid dispensed by a fluid infusion device is provided. The test system includes a test housing. The test housing includes an inlet and an internal channel. The inlet is to be coupled to the fluid infusion device to receive the volume of fluid, and the internal channel is in fluid communication with the inlet. The test system includes an input electrode coupled to the internal channel to be in fluid communication with the volume of fluid, and an output electrode coupled to the internal channel to be in fluid communication with the volume of fluid. The output electrode is coupled to the internal channel so as to be spaced apart from the input electrode. The test system includes a power source configured to create a voltage potential between the input electrode and the output electrode. The volume of fluid in the internal channel conducts current between the input electrode and the output electrode to facilitate measurement of the volume of fluid dispensed by the fluid infusion device.

Also provided according to various embodiments is a test system for measuring a volume of fluid dispensed by a fluid infusion device. The test system includes a test housing. The test housing includes an inlet and an internal channel. The inlet is to be coupled to the fluid infusion device to receive the volume of fluid, and the internal channel is in fluid communication with the inlet. The test system includes a plurality of input electrodes coupled to the internal channel to be in fluid communication with the volume of fluid, and a plurality of output electrodes coupled to the internal channel to be in fluid communication with the volume of fluid. The plurality of output electrodes is spaced apart from a respective one of the plurality of input electrodes. The test system includes a power source configured to apply a voltage to a respective one of the plurality of input electrodes. The volume of fluid in the internal channel conducts current between the respective one of plurality of input electrodes and a respective at least one of the plurality of output electrodes to facilitate measurement of the volume of fluid dispensed by the fluid infusion device.

Further provided is a test system for measuring a volume of fluid dispensed by a fluid infusion device. The test system includes a test housing. The test housing includes an inlet and an internal channel. The inlet is to be coupled to the fluid infusion device to receive the volume of fluid, and the internal channel is in fluid communication with the inlet. The test system includes a plurality of input electrodes coupled to the internal channel to be in fluid communication with the volume of fluid, and a plurality of output electrodes coupled to the internal channel to be in fluid communication with the volume of fluid. Each one of the plurality of output electrodes is spaced apart from a respective one of the plurality of input electrodes. The test system includes a power source configured to apply a voltage to a respective one of the plurality of input electrodes. The volume of fluid in the internal channel conducts current between a respective one of plurality of input electrodes and a respective at least one of the plurality of output electrodes to facilitate measurement of the volume of fluid dispensed by the fluid infusion device. Each of the plurality of input electrodes has an end that extends into the internal channel to be in communication with the fluid, and each of the plurality of output electrodes has a second end that extends into the internal channel that is spaced apart from the end of the respective one of the plurality of input electrodes such that a gap is defined within the internal channel between the end of the respective one of the plurality of input electrodes and the second end of respective one of the plurality of output electrodes.

Also provided according to various embodiments is a method for determining a volume of fluid dispensed into a test housing. The method includes controlling, by a processor, a power source to create a voltage potential across an input electrode arrangement and an output electrode arrangement associated with the input electrode arrangement each coupled to the test housing. The method includes receiving, by the processor, a signal from the output electrode arrangement based on the fluid received into the test housing, and calculating, by the processor, the volume of fluid dispensed into the test housing based on the signal received from the output electrode arrangement. The method includes generating, by the processor, a user interface for display on a display that illustrates the volume of fluid dispensed, and displaying the generated user interface on the display.

Further provided is a test control system for determining a volume of dispensed fluid. The test control system includes a test housing. The test housing includes an inlet and an internal channel. The inlet is to receive the volume of fluid, and the internal channel is in fluid communication with the inlet. The test control system includes an input electrode arrangement coupled to the test housing, and an output electrode arrangement associated with the input electrode arrangement and coupled to the test housing so as to be spaced apart from the input electrode arrangement. The test control system includes a controller, having a processor, that is configured to: control a power source to supply a voltage to the input electrode arrangement; receive a signal from the output electrode arrangement based on the fluid received into the test housing; calculate the volume of fluid dispensed into the test housing based on the signal received from the output electrode arrangement; generate a user interface for display on a display that illustrates the volume of fluid dispensed; and display the generated user interface on the display.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
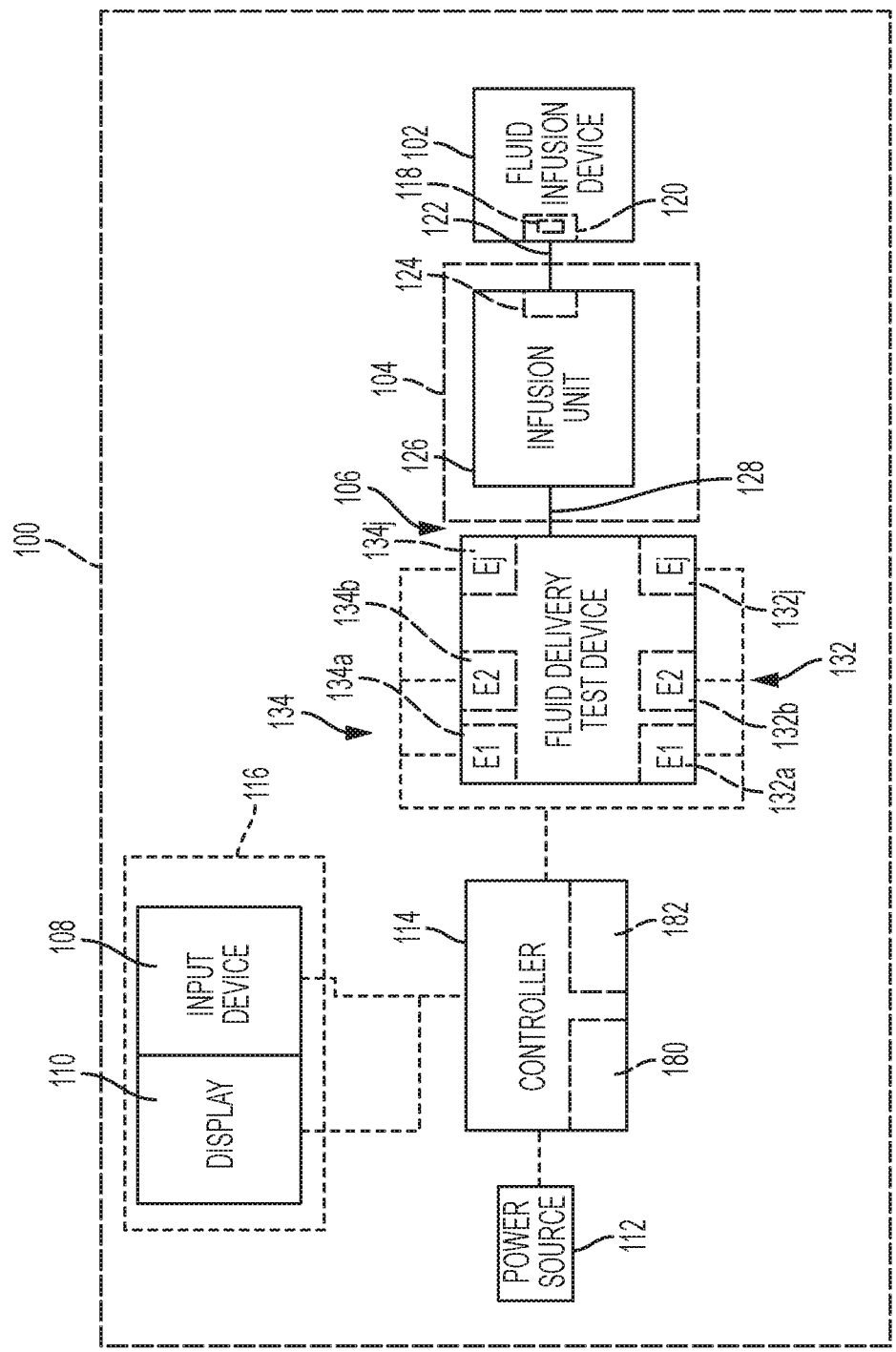
FIG. 1 is a functional block diagram illustrating an exemplary embodiment of a test system for electrofluidic measurement of a fluid delivery by a fluid infusion device according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of schematic, functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the test systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to various embodiments of a test system for measuring an amount of fluid delivered by a fluid infusion device to determine an accuracy of the fluid infusion device. The test system is a closed system, which is resistant to environmental factors, including temperature of the testing environment, evaporation, vibrations, humidity and air density. The test system provides a user interface to measure an amount of fluid dispensed by a variety of fluid infusion devices to determine a fluid delivery accuracy for the variety of fluid infusion devices, such as insulin infusion devices. The test system further enables precise and accurate measurement of the small amounts of fluid dispensed by the insulin infusion devices, including precise and accurate measurements for nanoliters and microliters dispensed by the insulin infusion devices, which may be used to determine an accuracy of the insulin infusion devices. It should be noted that while the test system is described herein as being used with an insulin infusion device, such as an insulin infusion pump, it will be understood that the test system may be employed with a variety of other fluid infusion devices and/or medical devices. Thus, while the non-limiting examples described below relate to a test system for use with a fluid infusion device used to treat diabetes, embodiments of the disclosed subject matter are not so limited.

With reference to FIG. 1, a functional block diagram of a test system 100 for measuring an amount of fluid delivered by a fluid infusion device 102 is shown. In this example, the test system 100 includes the fluid infusion device 102, an infusion set 104, a fluid delivery test device 106, an input device 108, a display 110, a power source 112 and a controller 114. The input device 108 and the display 110 are part of a human-machine interface 116. The human-machine interface 116 and the controller 114 may be associated with a computing device, such as a desktop computer, laptop computer, tablet or other computing device capable of receiving input, displaying output and controlling the fluid delivery test device 106. Generally, the test system 100 measures an amount of fluid dispensed by the fluid infusion device 102, compares the measured amount of fluid dispensed to the amount of fluid commanded to be dispensed by the fluid infusion device 102 and determines, based on the comparison, whether the amount of fluid delivered by the fluid infusion device 102 is accurate. In other embodiments, the test system 100 may be used to calibrate the fluid infusion device 102.

The fluid infusion device 102 dispenses a volume of a fluid 118 to the fluid delivery test device 106 through the infusion set 104. In one example, the fluid infusion device 102 is an insulin infusion device, such as an insulin infusion pump. As the fluid infusion device 102 comprises any suitable fluid infusion device known in the art, the fluid infusion device 102 will not be discussed in great detail herein. For example, the fluid infusion device 102 can comprise an insulin infusion device, such as the MiniMed™ 670G Insulin Pump System, the MiniMed Paradigm® REAL-Time Revel™ Insulin Pump, MiniMed™ 630G Insulin Pump System, MiniMed™ 530G Insulin Pump, MiniMed™ 640G Insulin Pump System each offered for sale by Medtronic MiniMed, Inc. of Northridge, Calif. Briefly, the fluid infusion device 102 is designed to be carried or worn by the patient. The fluid infusion device 102 may leverage a number of conventional features, components, elements, and characteristics described in U.S. Pat. Nos. 6,485,465 and 7,621,893, the relevant content of which is incorporated by reference herein. In addition, the fluid infusion device 102 may comprise the fluid infusion device described in U.S. Publication No. 2014/0207065, which is incorporated by reference herein.

Generally, the fluid infusion device 102 includes a fluid reservoir 120, which contains the fluid 118. Depending upon the particular fluid infusion device 102, the fluid reservoir 120 may be removably coupled to the fluid infusion device 102 or may be fixedly disposed within the fluid infusion device 102. In one example, the fluid reservoir 120 can comprise the fluid reservoir described in U.S. Publication No. 2014/0207065, which is incorporated by reference herein. It should be understood, however, that the fluid reservoir 120 can comprise any suitable fluid reservoir 120 that is capable of receiving and/or dispensing a fluid, and thus, the fluid reservoir 120 is merely an example. Generally, the fluid reservoir 120 is pre-filled with the fluid 118 prior to initiating a test, and the fluid infusion device 102 is primed prior to initiating the test.

In one example, the fluid 118 is an electrically conductive liquid. The fluid 118 is an electrolytic solution that has fluid properties that may be generally analogous to the fluid properties of insulin, for example, the fluid 118 is Newtonian and the surface energy of the fluid when interfacing with air is not greater than that of water interfacing with air. In this example, the fluid 118 is a potassium chloride (KCl) solution. It should be noted that any number of electrolytic solutions may be used for the fluid 118, including, but not limited to, a solution containing ammonium sulfate, calcium chloride, sodium chloride, potassium carbonate, sodium phosphate or other salt. In the example of the fluid 118 as comprising the potassium chloride solution, the fluid 118 has a concentration of about 2.5% by mass potassium chloride, which has a conductivity of about 29.5 millisiemens per centimeter (mS/cm). In one example, the fluid 118 may be employed in a test environment having a temperature of about 20 degrees Celsius (° C.).

The fluid infusion device 102 is controllable by an operator to dispense the fluid 118 from the fluid reservoir 120 in increments to perform the test. In one example, the operator or user controls the fluid infusion device 102, via a human-machine interface of the fluid infusion device 102, to dispense the fluid 118 from the fluid reservoir 120. As is generally known, the fluid infusion device 102 includes one or more input devices, which enable the operator to select an amount of the fluid 118 to be dispensed from the fluid reservoir 120 by the fluid infusion device 102. For example, the operator may select to dispense the fluid 118 in increments or boluses of a pre-defined discrete volume or at a volume of fluid for a particular period of time (basal rate). For example, a pre-defined volume for a bolus may be about 250 nanoliters (nL). The amount of the fluid 118 selected to be dispensed by the operator of the fluid infusion device 102 may be input to the controller 114 via the human-machine interface 116. In one example, for each command input by the operator to the fluid infusion device 102 to dispense an increment of the fluid 118, the operator may input the commanded increment via the human-machine interface 116 to the controller 114. In certain embodiments, the controller 114 may communicate directly with the fluid infusion device 102, over a suitable wireless communication protocol, and may command the fluid infusion device 102 to dispense the fluid 118 at a particular increment.

The infusion set 104 is fluidly coupled to the fluid reservoir 120 of the fluid infusion device 102. As the infusion set 104 comprises any suitable fluid infusion set known in the art, the infusion set 104 will not be discussed in great detail herein. For example, the infusion set 104 can comprise an insulin infusion set, such as the MiniMed Quick-set® infusion set offered for sale by Medtronic MiniMed, Inc. of Northridge, Calif. In one example, the infusion set 104 includes a flexible tubing or conduit 122, which is coupled at one end to a set connector 124 and is coupled at an opposite end to an infusion unit 126. The set connector 124 defines a fluid flow path for the fluid 118 from the fluid reservoir 120. The infusion unit 126 is fluidly coupled to the conduit 122 at a distal end of the conduit 122 and provides a fluid pathway from the fluid reservoir 120 to the body of the patient. The infusion unit 126 generally includes a fluid outlet or cannula 128. In this example, the cannula 128 is fluidly coupled to the fluid delivery test device 106 to deliver the fluid 118 from the fluid reservoir 120 to the fluid delivery test device 106.

The fluid delivery test device 106 is in fluid communication with the fluid reservoir 120 to receive the fluid 118 via the infusion set 104. Stated another way, the fluid delivery test device 106 receives the fluid 118 from the fluid infusion device 102, which is communicated through the fluid flow path defined by the infusion set 104. The fluid delivery test device 106 is also in communication with the controller 114 and the power source 112. In one example, the fluid delivery test device 106 includes a test housing 130, a plurality of input electrodes 132 and a plurality of output electrodes 134.

Figure 2:
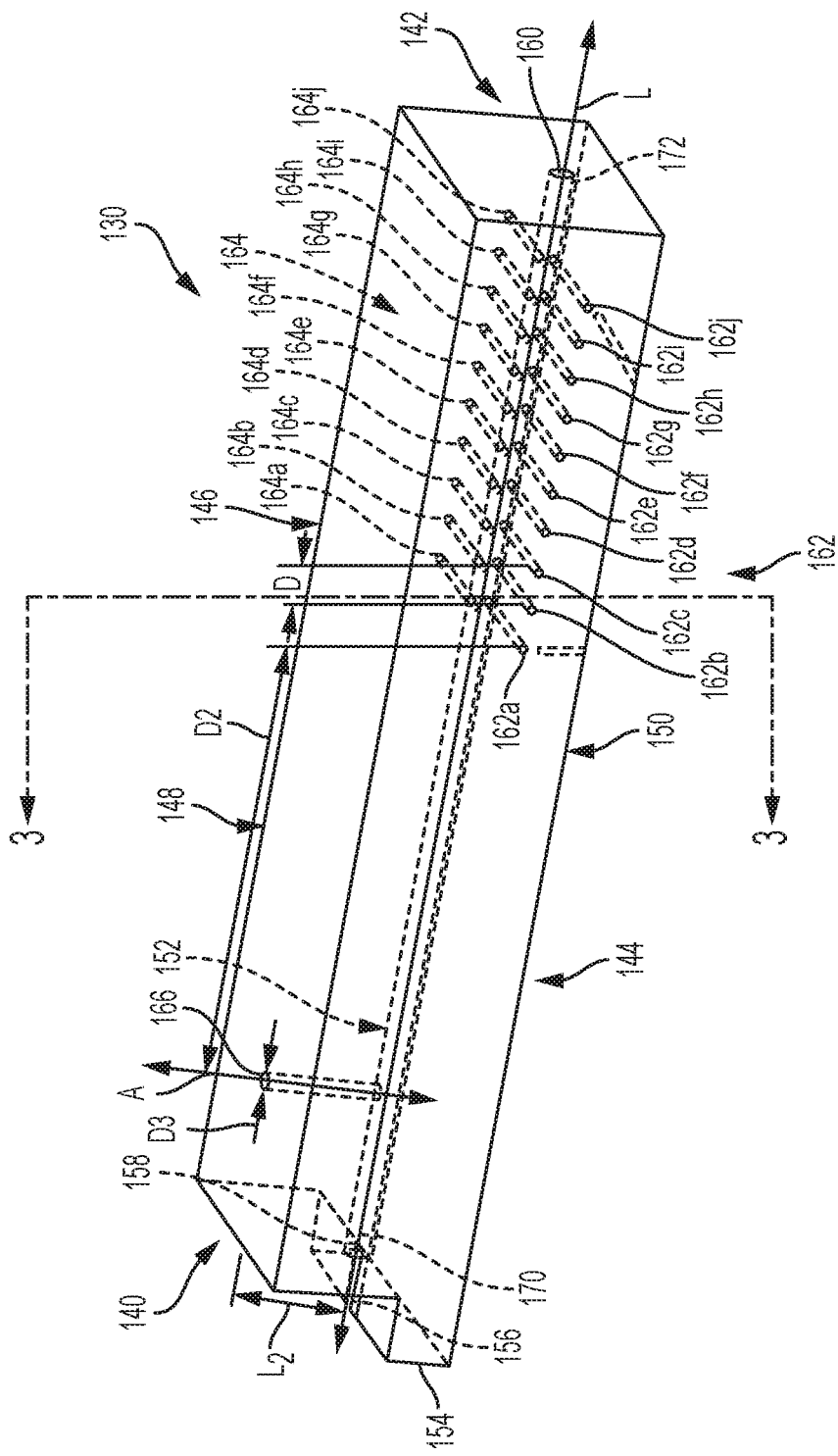
FIG. 2 is a perspective view of a test housing of the test system of FIG. 1.

With reference to FIG. 2, the test housing 130 is shown with the input electrodes 132 and the output electrodes 134 removed for clarity. As shown in FIG. 2, the test housing 130 is integrally formed, monolithic or one-piece. The test housing 130 may be composed of a non-conductive material. In this example, the test housing 130 is composed of a polymer-based material, including, but not limited to, Poly-jet VeroClear material. The test housing 130 may be formed through 3D printing or other additive manufacturing techniques, or may be machined, cast, molded, etc. The test housing 130 includes a first housing end 140 opposite a second housing end 142, a first housing side 144 opposite a second housing side 146, a first housing surface 148 opposite a second housing surface 150 and an internal channel 152.

In one example, the first housing end 140 is stepped, and includes a projection 154. It should be noted, however, that the first housing end 140 may be substantially planar or flat. In this example, the projection 154 defines a cleaning inlet 156. The cleaning inlet 156 is defined on a surface 154a of the projection 154. The cleaning inlet 156 is in fluid communication with an inlet 158 of the internal channel 152. The cleaning inlet 156 enables the internal channel 152 to be cleaned or prepared for another test. For example, a cleaning fluid, such as compressed air or a liquid cleaning solution may be used to remove the fluid 118 (FIG. 1) from the test housing 130.

The second housing end 142 is substantially flat or planar, and defines an outlet port 160. The outlet port 160 is in fluid communication with the internal channel 152, and enables the fluid 118 and the cleaning fluid, to exit the internal channel 152 and the test housing 130.

The first housing side 144 interconnects the first housing end 140 and the second housing end 142. The first housing side 144 defines a plurality of input electrode bores 162. In one example, the first housing side 144 defines about 10 input electrode bores 162a-162j. It should be noted; however, that the first housing side 144 can define any number of input electrode bores 162a . . . 162n. Each of the input electrode bores 162a-162j receives a respective one of the plurality of input electrodes 132. In this example, each of the input electrode bores 162a-162j is circular or cylindrical, and is in communication with the internal channel 152. Each of the input electrodes 132a-132j are spaced a predetermined distance D apart, and thus, each of the input electrode bores 162a-162j are also spaced a predetermined distance apart to accommodate the distance D between each of the input electrodes 132a-132j. In one example, in order to determine the distance D between each of the input electrodes 132a-132j, the following equation is used:

$$(D \pm x_2) = \frac{v_m}{(A_c \pm x_1)} - W_e \qquad (1)$$

Wherein, $A_c$ is the cross-sectional area of the internal channel 152 in millimeters (mm); $x_1$ is the manufacturing tolerance associated with the cross-sectional area of the internal channel 152, which in one example, is a manufacturing tolerance associated with the width and the height of the internal channel 152 (in the example of a cylindrical internal channel 152, $x_1$ is the manufacturing tolerance associated with the radius ($R_c$) of the internal channel 152); $x_2$ is the manufacturing tolerance associated with the spacing between each of the input electrodes 132a-132j and each of the output electrodes 134a-134j, respectively; $W_e$ is the thickness of the input electrodes 132a-132j and the output electrodes 134a-134j in millimeters (mm), which in this example is the same; $V_m$ is the minimum resolution of fluid volume that is desired to be measured or observed by the output electrode 134a-134j of the test system 100 in microliters (μL); and D is the distance between each of the input electrodes 132a-132j and each of output electrodes 134a-134j, respectively, of the test housing 130 (measured between respective ends 174a-174j; 176a-176j) in millimeters (mm), which in this example is the same. In one example, the distance D is about 2.86 millimeters (mm) to about 3.49 millimeters (mm), based on a radius $R_c$ (FIG. 3) of the internal channel 152 of about 0.87 millimeters (mm) to about 1.06 millimeters (mm) and a desired measured volume $V_m$ of 10 microliters (μL). In one example, the distance D is greater than the radius $R_c$; however, in other examples, the distance D may be equal to or less than the radius $R_c$. In other examples, the first housing side 144 need not include the plurality of input electrode bores 162, rather, wiring for the plurality of input electrodes 132 may be internal to or contained within the test housing 130. Based on the distance D and the known thickness $W_e$ of the input electrodes 132a-132j, each of the input electrode bores 162a-162j are defined a predetermined distance apart to ensure the distance D between each of the input electrodes 132a-132j is maintained.

The second housing side 146 interconnects the first housing end 140 and the second housing end 142. The second housing side 146 defines a plurality of output electrode bores 164. In one example, the second housing side 146 defines about 10 output electrode bores 164a-164j. It should be noted; however, that the second housing side 146 can define any number of output electrode bores 164a . . . 164n. Each of the output electrode bores 164a-164j receives a respective one of the plurality of output electrodes 134. In this example, each of the output electrode bores 164a-164j is circular or cylindrical, and is in communication with the internal channel 152. In other examples, the second housing side 146 need not include the plurality of output electrode bores 164, rather, wiring for the plurality of output electrodes 134 may be internal to or contained within the test housing 130.

Each of the output electrode bores 164a-164j is associated with a respective one of the input electrode bores 162a-162j and each of the output electrode bores 164a-164j is also spaced the predetermined distance apart to accommodate the spacing of the output electrodes 134a-134j the predetermined distance D apart. Based on the distance D and the known thickness $W_e$ of the output electrodes 134a-134j, each of the output electrode bores 164a-164j are defined a predetermined distance apart to ensure the distance D between each of the output electrodes 134a-134j is maintained. As will be discussed, by spacing each of the input electrodes 132a-132j and each of the output electrodes 134a-134j, respectively, apart by the predetermined distance D, an amount or volume of the fluid 118 dispensed by the fluid infusion device 102 may be determined by the controller 114. Generally, each of the output electrode bores 164a-164j is offset from a respective one of the input electrode bores 162a-162j. In this regard, in this example, the input electrode bores 162a-162j are defined such that each one of the input electrode bores 162a-162j is defined between a respective pair of the output electrode bores 164a-164j. Generally, each input electrode bore 162a-162j is defined halfway between adjacent ones of the plurality of output electrode bores 164a-164j, which doubles a resolution of a signal received from the plurality of output electrodes 134. In this example, the plurality of input electrode bores 162a-162j and the plurality of output electrode bores 164a-164j are defined in the test housing 130 so as to be near or proximate the second housing end 142.

The first housing surface 148 interconnects the first housing side 144 and the second housing side 146; and interconnects the first housing end 140 and the second housing end 142. The first housing surface 148 is substantially planar or flat, and defines an infusion set inlet port 166. In this example, the infusion set inlet port 166 is defined near or proximate the first housing end 140. The infusion set inlet port 166 is sized and configured to receive the cannula 128. In one example, the infusion set inlet port 166 is substantially cylindrical, and is sized to have a clearance fit with the cannula 128. It should be noted that in other embodiments, the infusion set inlet port 166 may include a septum or have an interference fit with the cannula 128 to provide a fluid seal between the cannula 128 and the test housing 130, which inhibits fluid, such as air, from entering the test housing 130. In one example, the infusion set inlet port 166 has a diameter D3 of about 1.27 millimeters (mm) and a length L2 of about 9.0 millimeters (mm).

The infusion set inlet port 166 is in fluid communication with the internal channel 152 to provide a fluid flow path from the fluid infusion device 102 via the infusion set 104 into the test housing 130. As will be discussed, the fluid 118 received from the cannula 128 of the infusion set 104 flows into the internal channel 152 to determine an amount of the fluid 118 or a volume of the fluid 118 dispensed by the fluid infusion device 102. The infusion set inlet port 166 is generally defined through the first housing surface 148 so as to be spaced a distance D2 apart from the input electrode bore 162a and the output electrode bore 164a. In one example, the distance D2 is about 1.5 millimeters to about 3.5 millimeters (mm), which provides a buffer before the fluid 118 contacts the plurality of input electrodes 132 and the plurality of output electrodes 134. The distance D2 also serves as a priming distance, which enables the fluid infusion device 102 and the test housing 130 to be primed with the fluid 118 prior to the starting of a test. The infusion set inlet port 166 is also defined so as to extend along an axis A, which is substantially perpendicular to a longitudinal axis L of the test housing 130. The first housing surface 148 also provides a surface for positioning or resting the infusion set 104 on the test housing 130. The second housing surface 150 interconnects the first housing side 144 and the second housing side 146; and interconnects the first housing end 140 and the second housing end 142. The second housing surface 150 is substantially planar or flat.

The internal channel 152 is defined through the test housing 130 from the first housing side 140 to the second housing side 142. In one example, the internal channel 152 is defined so as to extend along linearly along the longitudinal axis L of the test housing 130. The internal channel 152 extends from a first channel end 170 to a second channel end 172. The first channel end 170 is in fluid communication with the cleaning inlet 156, and the second channel end 172 is in fluid communication with the outlet port 160. The internal channel 152 is also in fluid communication with the infusion set inlet port 166, each of the plurality of input electrode bores 162a-162j and each of the plurality of output electrode bores 164a-164j. Generally, with reference to FIG. 3, the internal channel 152 is cylindrical. The plurality of input electrode bores 162a-162j and the plurality of output electrode bores 164a-164j intersect a diameter of the internal channel 152 and are positioned on opposite sides of the internal channel 152. In one example, the internal channel 152 has a length L3, which is sized to enable a predetermined number of volume measurements of the fluid 118. In this example, the internal channel 152 has a length L3 of about 31.2 millimeters (mm) to about 32.2 millimeters (mm), which enables about 10 measurements of about 0.01 milliliters (mL) (10 microliters (μL)). Generally, the fluid 118 is received in the internal channel 152 such that in order for the fluid 118 to move along the internal channel 152, additional fluid 118 must be received through the infusion set inlet port 166. Thus, each of the input and output electrodes 132a, 134a; 132b, 134b . . . 132j, 134j is capable of measuring a discrete volume of fluid received through the infusion set inlet port 166. In certain embodiments, the internal channel 152 may be defined as a discrete component, which is positioned within the test housing 130 instead of being monolithically, integrally formed with or integrally defined within the test housing 130. For example, depending upon the size of the measurements required by the test housing 130, the internal channel 152 may be etched onto a glass substrate and coated with a hydrophobic finish. The glass substrate comprising the internal channel 152 may then be coupled within the test housing 130, via adhesives, ultrasonic welding, mechanical fasteners, etc.

Figure 3:
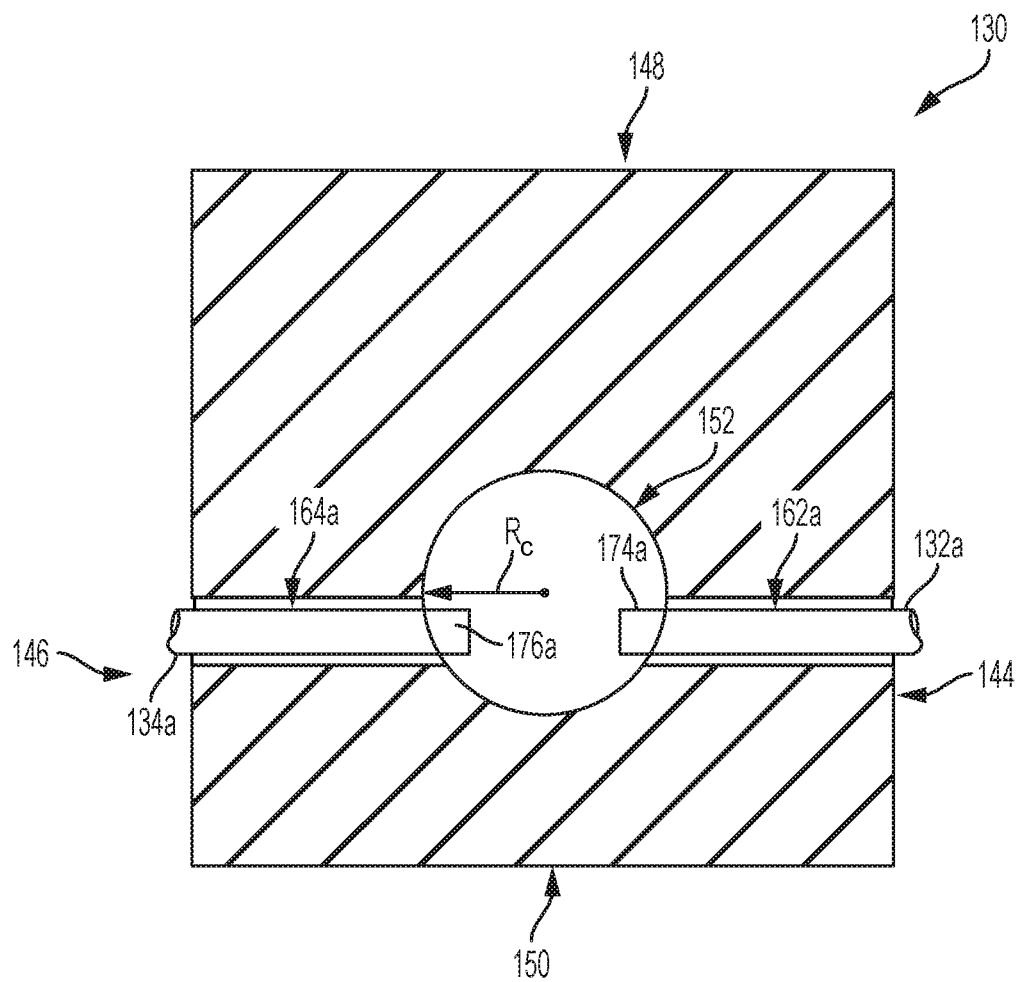
FIG. 3 is a cross-sectional view of the test housing, taken along line 3-3 of FIG. 2.

With reference back to FIG. 1, each of the plurality of input electrodes 132 receives current at a particular voltage from the power source 112, and each of the plurality of input electrodes 132 is in communication with the power source 112 to receive the current at the particular voltage. In one example, the input voltage is about 1.0 volts (V). It should be noted, however, that another suitable voltage may be used. In this example, the plurality of input electrodes 132 include 10 input electrodes 132a-132j, which are received in a respective one of the input electrode bores 162a-162j. It should be noted that the fluid delivery test device 106 may include any number of input electrodes 132a . . . 132n, and a corresponding number of input electrode bores 162a . . . 162n. In this example, each of the input electrodes 132a-132j comprises conductive wire. In one example, each of the input electrodes 132a-132j comprise 30 gauge electrical wire, with one end of the input electrode 132a-132j received in a respective one of the input electrode bores 162a-162j, and the opposite end of the input electrode 132a-132j coupled to and in communication with the power source 112 to receive the input current at the particular voltage. In one example, a thickness $W_e$ of each of the input electrodes 132a-132j is about 0.24 millimeters (mm) to about 0.26 millimeters (mm). With reference to FIG. 3, an end 174a of the input electrode 132a is shown received within the internal channel 152. Generally, for each of the input electrodes 132a-132j, the end 174a-174j is received within the internal channel 152 so as to be in contact with and in fluid communication with the fluid 118 received within the internal channel 152. It should be noted that the input electrodes 132a-132j need not comprise electrical wire, but rather, any suitable electrode may be employed, including, but not limited to, flat panel electrodes. In the example of flat panel input electrodes, the flat panel input electrodes may be coupled to sidewalls of the internal channel 152.

Each of the plurality of output electrodes 134 receive as input the current applied to the respective one of the input electrodes 132a-132j as conducted by the fluid 118 within the internal channel 152. Each of the plurality of output electrodes 134 is in communication with the controller 114 and outputs a signal based on current received from the respective input electrodes 132a-132j through the fluid 118. Stated another way, each of the output electrodes 134 is in communication with the fluid 118 to receive the current applied to the respective input electrode 132a-132j through the fluid 118, and to transmit a signal to the controller 114 that the current has been received. In other words, a pair of electrodes that comprises an input electrode 132a-132j and an output electrode 134a-134j is spaced apart by the internal channel 152 that forms an open switch. In this example, the output electrodes 134a-134j are connected to ground. When the fluid 118 is received within the internal channel 152 and is in communication with the respective input electrode 132a-132j and the respective one or more output electrodes 134a-134j, the fluid 118 closes the switch, allowing the current applied to the respective input electrode 132a-132j to transfer through the fluid 118 to the respective one or more output electrodes 134a-134j, which results in a current reading or signal being communicated to the controller 114. Thus, an open circuit (air between the input electrodes 132a-132j and the output electrodes 134a-134j) yields a signal of zero, and a closed circuit (electrolytic fluid between the input electrodes 132a-132j and the output electrodes 134a-134j) yields a signal of about 1.0 volt (V) and indicates that the fluid 118 has reached a particular output electrode 134a-134j.

In this example, the plurality of output electrodes 134 include 10 output electrodes 134a-134j, which are received in a respective one of the output electrode bores 164a-164j. It should be noted that the fluid delivery test device 106 may include any number of output electrodes 134a . . . 134n that correspond to a respective number of input electrodes 132a . . . 132n, and a corresponding number of output electrode bores 162a . . . 162n. In this example, each of the output electrodes 134a-134j comprises conductive wire. In one example, each of the output electrodes 134a-134j comprise 30 gauge electrical wire, with one end of the output electrodes 134a-134j received in a respective one of the output electrode bores 164a-164j, and the opposite end of the output electrodes 134a-134j coupled to and in communication with the controller 114 to provide the controller 114 with a signal or the current received. In this example, each of the output electrodes 134a-134j is associated with a respective input port of the controller 114 such that the controller 114 is able to identify the particular output electrode 134a-134j the current or signal is received from. Generally, a thickness $W_e$ of each of the output electrodes 134a-134j is the same as the $W_e$ of each of the input electrodes 132a-132j, and in this example, is about 0.24 millimeters (mm) to about 0.26 millimeters (mm). It should be noted that the output electrodes 134a-134j need not comprise electrical wire, but rather, any suitable electrode may be employed, including, but not limited to, flat panel electrodes. In the example of flat panel output electrodes, the flat panel output electrodes may be coupled to sidewalls of the internal channel 152.

With reference to FIG. 3, an end 176a of the output electrode 134a is shown received within the internal channel 152. Generally, for each of the output electrodes 134a-134j, the end 176a-176j is received within the internal channel 152 so as to be in contact with and in fluid communication with the fluid 118 received within the internal channel 152. In this example, the end 176a-176j of the respective output electrode 134a-134j is spaced apart from the end 174a-174j of the respective input electrode 132a-132j such that a gap is defined between the respective end 174a-174j and end 176a-176j when the fluid 118 is not disposed between or is devoid from being between the respective input and output electrodes 132a-132j; 134a-134j within the internal channel 152. The gap prevents or inhibits a flow of current from the respective input electrode 132a-132j to the respective one or more output electrodes 134a-134j. In this example, the gap is filled with air; however, another electrically insulating medium that is hydrophobic may be used.

With reference back to FIG. 1, the input device 108 and the display 110 form the human-machine interface 116. Each of the input device 108 and the display 110 are in communication with the controller 114 via a suitable communication medium, such as a bus. The input device 108 may be configured in a variety of ways. In some embodiments, the input device 108 may include various switches or levers, one or more buttons, a touchscreen interface that may be overlaid on the display 110, a keyboard, an audible device, a microphone associated with a speech recognition system, or various other human-machine interface devices.

The display 110 comprises any suitable technology for displaying information, including, but not limited to, a liquid crystal display (LCD), organic light emitting diode (OLED), plasma, or a cathode ray tube (CRT). In this example, the display 110 is an electronic display capable of graphically displaying one or more user interfaces under the control of the controller 114. Those skilled in the art may realize other techniques to implement the display 110 in the test system 100.

The power source 112 is in communication with the controller 114, over a suitable communication medium, such as a bus. The power source 112 provides a current at a particular voltage to the input electrodes 132a-132j. Generally, the power source 112 creates a voltage potential between the input electrodes 132a-132j and the output electrodes 134a-134j (as the output electrodes 134a-134j are tied to ground) when the fluid 118 is present, which causes current to flow between the respective input electrode 132a-132j and the respective output electrode 134a-134j in the internal channel 152. In one example, the power source 112 includes a direct current (DC) source. In this example, the power source 112 outputs a 5 volt (V) pulse width modulation wave, which is reduced to the about 1 volt (V) input voltage with a voltage divider. Alternatively, an H-bridge may also be employed to invert the pulse width modulation wave to increase the input voltage, if desired. In one example, the voltage divider includes two resistors, with one having a resistance of about 3.3 M ohms and the other resistor having a resistance of 1.0 M ohms. In one example, the pulse width is about 0.01% and the frequency is about 5 Hertz (Hz), which reduces clustering of the ions in the fluid 118 about the respective output electrode 134a-134j. Generally, the power source 112 applies the voltage to each of the input electrodes 132a-132j to create a voltage potential between the input electrodes 132a-132j and the output electrodes 134a-134j in an alternating pattern to enable the ions in the fluid 118 to "reset" and prevent clustering of the electrolytes in the fluid 118 onto the output electrode 134a-134j, which inhibits the flow of the fluid 118. This enables the current to flow through the fluid 118 for a longer period of time. In one example, the power source 112 applies the input voltage to the input electrode 132a and establishes a voltage potential between the input electrode 132a and the output electrode 134a, then the power source 112 applies the input voltage to the input electrode 132b and establishes a voltage potential between the input electrode 132b and the output electrode 134b, etc., until the input voltage has been applied to the input electrode 132j and establishes a voltage potential between the input electrode 132j and the output electrode 134j; and then the power source 112 returns to apply the input voltage to the input electrode 132a. Thus, the power source 112 is configured to apply the voltage to a respective one of the input electrodes 132a-132j in a sequential pattern; however, it will be understood that the power source 112 may apply the voltage to the input electrodes 132a-132j in any pattern that reduces the clustering of the ions of the fluid 118 about the output electrodes 134a-134j.

Generally, the output electrodes 134a-134j read a voltage of either 0 volts (V) or approximately 1.0 volts (V) depending on whether current is flowing through them. In this example, this signal from the output electrodes 134a-134j requires amplification since the cutoff for reading digital HIGH by at least one processor 180 of the controller 114 is 3.3V. In order to amplify this signal, in this example, the output electrodes 134a-134j are each electrically connected to standard Operational Amplifier voltage comparator circuits, such as, for example Operational Amplifier OPA2336, which is commercially available from Texas Instruments, Inc. of Dallas, Tex. The signal of each of the output electrodes 134a-134j is compared to a reference voltage of 0.5 volt (V). If the voltage from the output electrodes 134a-134j exceeds the reference voltage, the Operational Amplifier outputs a digital HIGH, and processor 180 determines that the fluid 118 is at the site of that particular output electrode 134a-134j in the internal channel 152.

Generally, the distance D between each of the input electrodes 132a-132j and each of the output electrodes 134a-134j combined with the dimensions of the internal channel 152 provide the minimum resolution of this test system 100. In this example, the input electrodes 132a-132j, the output electrodes 134a-134j and their spacing are analogous the graduations on a ruler. The number of graduations (the input electrodes 132a-132j and the output electrodes 134a-134j) and the distance D each of the input electrodes 132a-132j and each of the output electrodes 134a-134j are spaced apart from another, respectively, generally dictates how small or large an amount may be measured. For example, in order to measure 1.0 microliters (μL), the test system 100 would include ten graduations or ten input electrodes 132a-132j and ten output electrodes 134a-134j that are each able to measure 0.1 microliter (μL).

The controller 114 includes the processor 180 and a computer readable storage device or media 182. The processor 180 can be any custom made or commercially available processor, a central processing unit (CPU), a graphics processing unit (GPU), an auxiliary processor among several processors associated with the controller 114, a semiconductor based microprocessor (in the form of a microchip or chip set), a macroprocessor, any combination thereof, or generally any device for executing instructions. The computer readable storage device or media 182 may include volatile and nonvolatile storage in read-only memory (ROM), random-access memory (RAM), and keep-alive memory (KAM), for example. KAM is a persistent or non-volatile memory that may be used to store various operating variables while the processor 180 is powered down. The computer-readable storage device or media 182 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 114 in controlling components associated with the test system 100.

The instructions may include one or more separate programs, each of which comprises an ordered listing of executable instructions for implementing logical functions. The instructions, when executed by the processor 180, receive and process input signals, perform logic, calculations, methods and/or algorithms for controlling the components of the test system 100, and generate control signals to components of the test system 100 to determine an amount of the fluid 118 dispensed by the fluid infusion device 102 based on the logic, calculations, methods, and/or algorithms. Although only one controller 114 is shown in FIG. 1, embodiments of the test system 100 can include any number of controllers 114 that communicate over any suitable communication medium or a combination of communication mediums and that cooperate to process the sensor signals, perform logic, calculations, methods, and/or algorithms, and generate control signals to control features of the test system 100.

In various embodiments, one or more instructions of the controller 114 are associated with the test system 100 and, when executed by the processor 180, the instructions receive and process signals from the human-machine interface 116 to test the accuracy of the fluid infusion device 102. For example, as will be discussed herein, the instructions of the controller 114, when executed by the processor 180, determine whether to perform a bolus test, a basal test or to calibrate the test housing 130. In various embodiments, the instructions of the controller 114 determine an amount of the fluid 118 or volume of the fluid 118 dispensed by the fluid infusion device 102, and output one or more user interfaces for display on the display 54 of the human-machine interface 116 that illustrate the volume of the fluid 118 dispensed by the fluid infusion device 102 over time. In various embodiments, the instructions of the controller 114 determine the output electrode 134a-134j activated by the fluid dispensed by the fluid infusion device 102, and output one or more user interfaces for display on the display 54 of the human-machine interface 116 that illustrate the number of output electrodes 134a-134j activated by the fluid over time.

Generally, prior to performing a test using the test housing 130, the fluid reservoir 120 of the fluid infusion device 102 is pre-filled with the fluid 118, and the fluid reservoir 120 is coupled to the fluid infusion device 102. The infusion set 104 is coupled to the fluid reservoir 120, and generally, the fluid infusion device 102, to define a fluid flow path from the fluid reservoir 120. The infusion unit 126 is coupled to the first housing surface 148 of the test housing 130 such that the cannula 128 is received within and coupled to the infusion set inlet port 166. With the fluid infusion device 102 fluidly coupled to the test housing 130, the user may initiate a test of the delivery volume accuracy of fluid infusion device 102 and/or may initiate a calibration test to calibrate the test housing 130. In one example, the fluid infusion device 102 is primed with the fluid 118, and the test housing 130 is also at least partially primed with the fluid 118 prior to the calibration test or the test of the delivery volume accuracy.

Figure 4A:
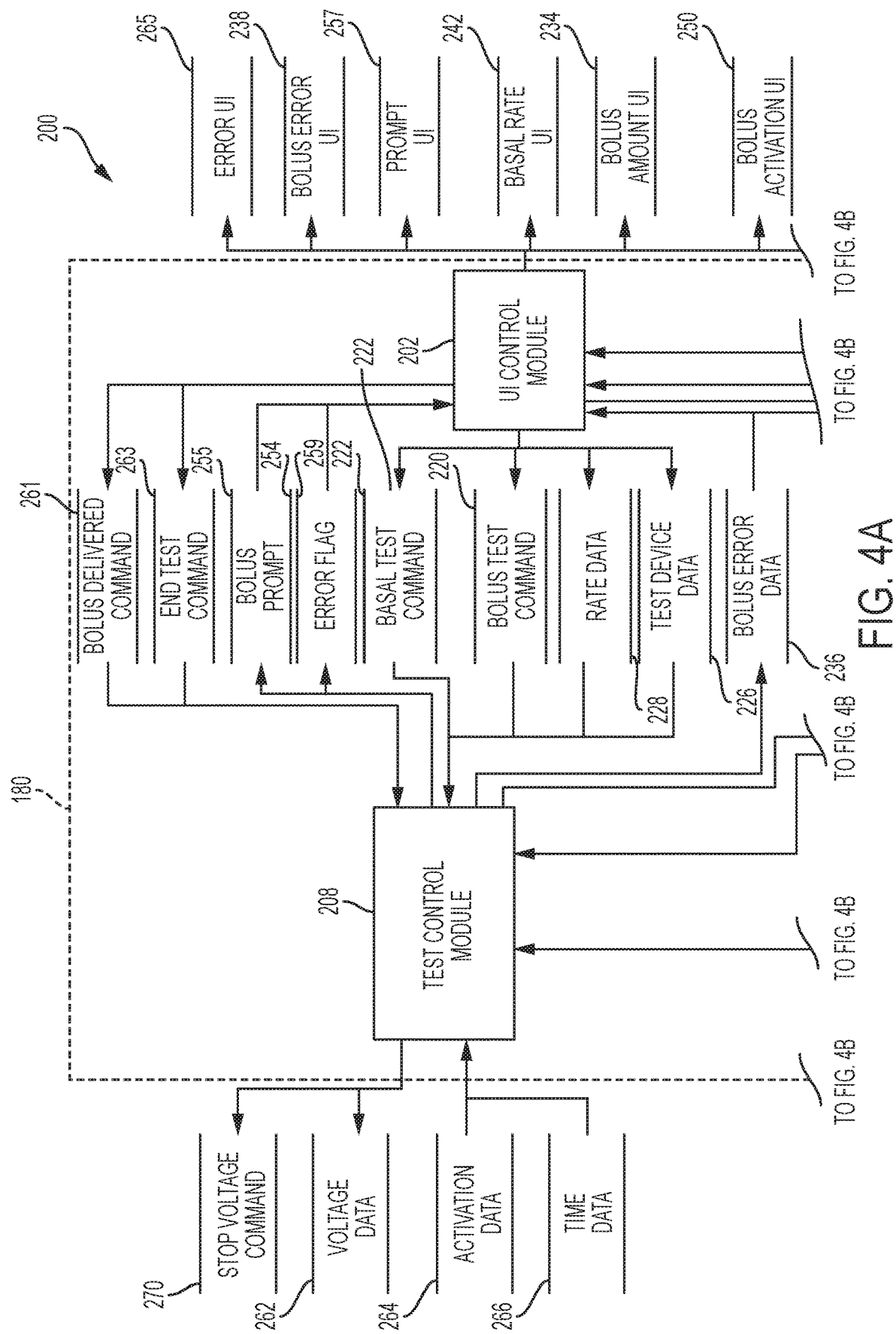
FIG. 4A is a dataflow diagram illustrating a test control system of the test system of FIG. 1, in accordance with various embodiments.
Figure 4B:
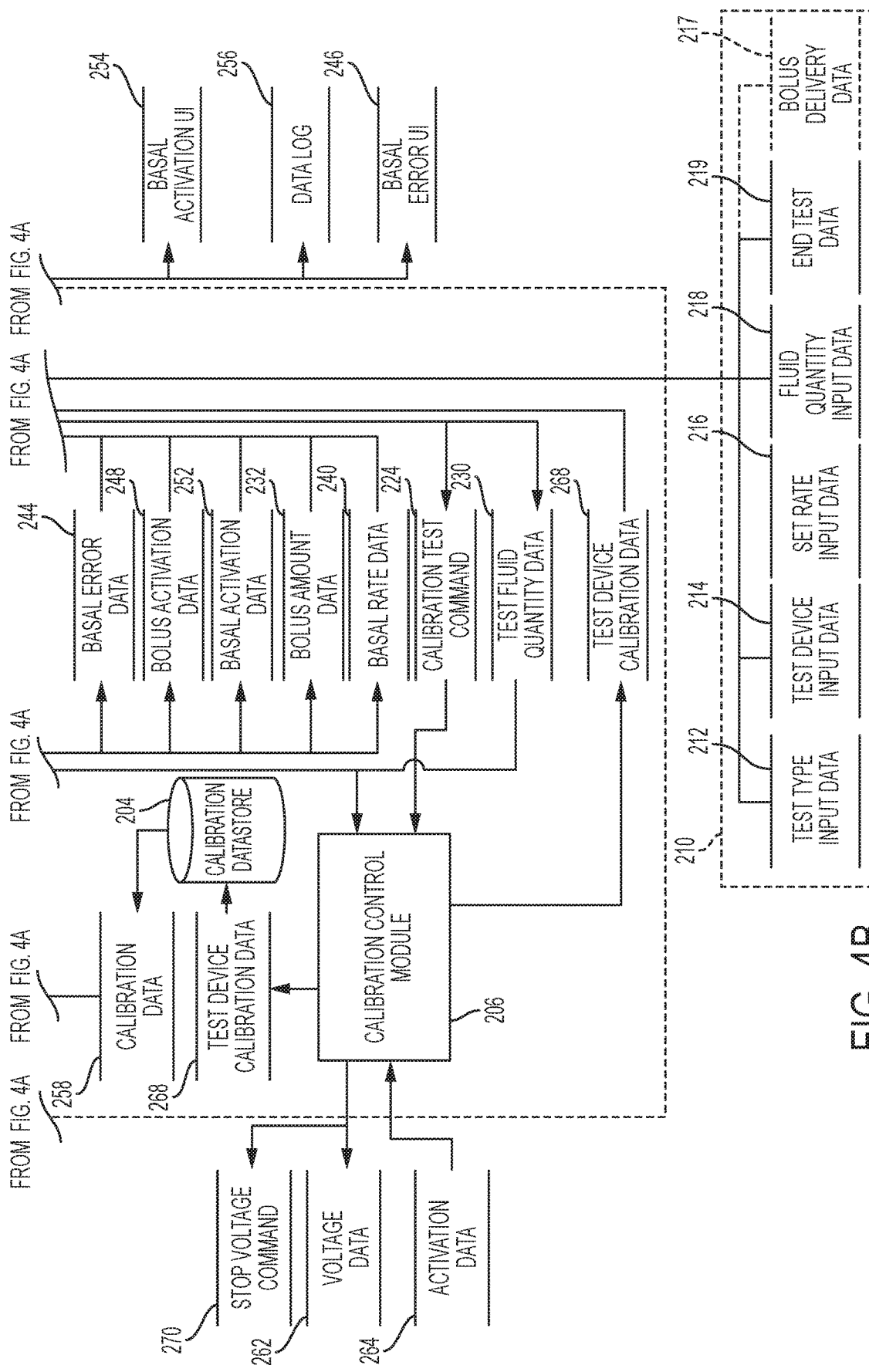
FIG. 4B is a continuation of the dataflow diagram of FIG. 4A.
Figure 5:
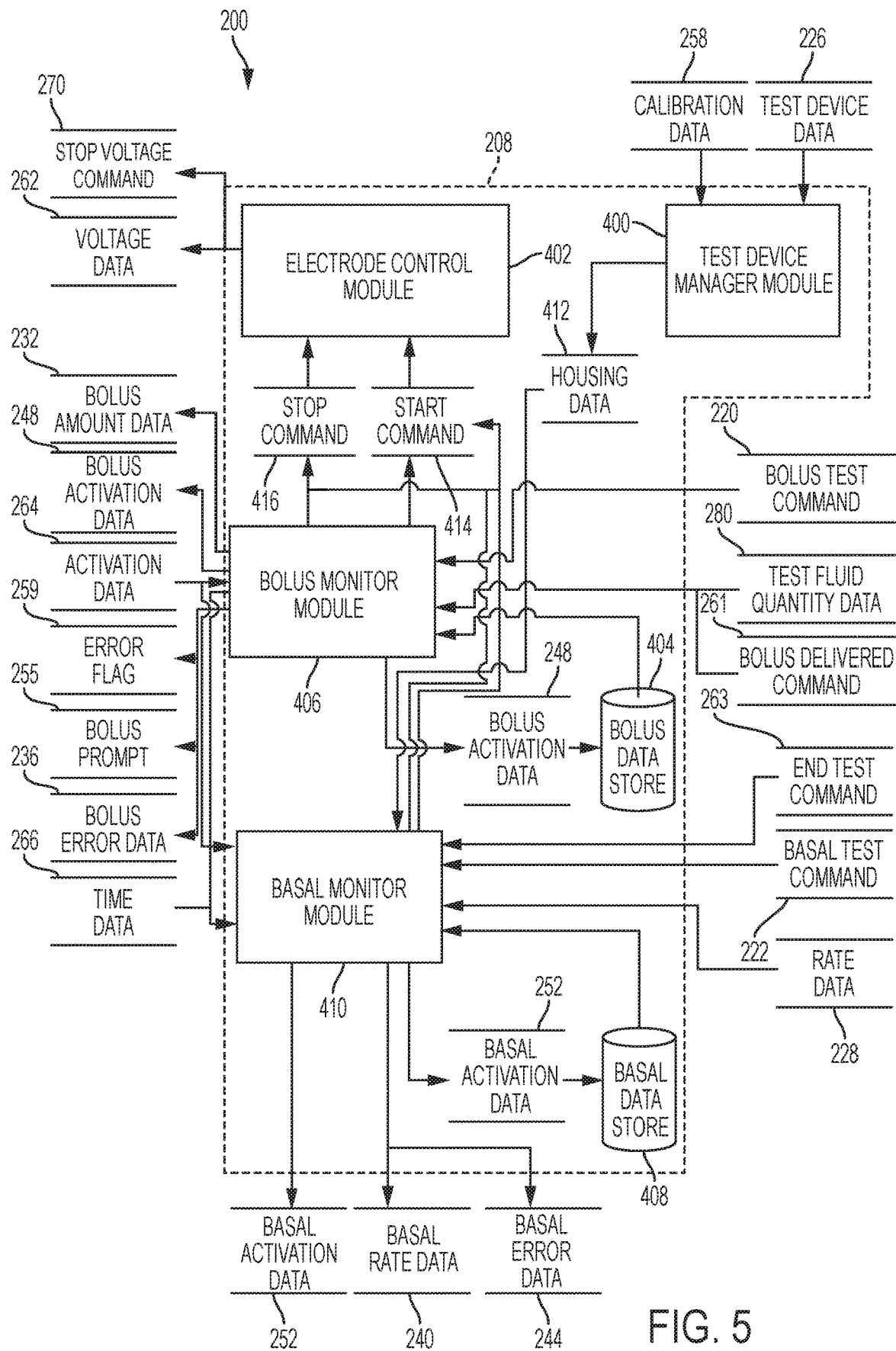
FIG. 5 is a dataflow diagram illustrating a test control module of the test control system of FIGS. 4A and 4B, in accordance with various embodiments.

For example, as shown in more detail with regard to FIGS. 4 and 5, and with continued reference to FIG. 1, dataflow diagrams illustrate various embodiments of a test control system 200 of the test system 100, which may be embedded within the controller 114. Various embodiments of the test control system 200 according to the present disclosure can include any number of sub-modules embedded within the controller 114. As can be appreciated, the sub-modules shown in FIGS. 4 and 5 may be combined and/or further partitioned to similarly control the input electrodes 132a-132j and determine an amount of fluid dispensed by the fluid infusion device 102 based on the activated output electrode 134a-134j. Inputs to the test control system 200 may be received from the human-machine interface 116 (FIG. 1), received from the output electrodes 134a-134j (FIG. 1), received from other control modules (not shown) associated with the test system 100, and/or determined/modeled by other sub-modules (not shown) within the controller 114. In various embodiments, with reference to FIGS. 4A and 4B, the test control system 200 includes a user interface (UI) control module 202, a calibration datastore 204, a calibration control module 206 and a test control module 208.

The user interface (UI) control module 202 receives input data 210. The input data 210 is received from a user's interaction with the human-machine interface 116 (FIG. 1). In one example, the input data 210 comprises test type input data 212, test device input data 214, set rate input data 216, bolus delivery data 217, fluid quantity input data 218 and end test data 219. The test type input data 212 is a type of test to be performed with the test system 100, and includes, but is not limited to, a selection of a bolus test, a basal test and a calibration test. The test device input data 214 includes a unique identifier associated with a particular test housing 130; the distance D between each of the input electrodes 132a-132j and each of the output electrodes 134a-134j, respectively, of the test housing 130; the radius $R_c$ of the cross-sectional area of the internal channel 152 or the cross sectional area $A_c$ of the internal channel 152; a thickness $W_e$ of the input electrodes 132a-132j and the output electrodes 134a-134j; a manufacturing tolerance associated with the spacing between each of the input electrodes 132a-132j; a manufacturing tolerance associated with the radius $R_c$ of the cross-sectional area of the internal channel 152 or a manufacturing tolerance associated with the cross-sectional area $A_c$ of the internal channel 152 (such as a manufacturing tolerance associated with a height and a width of the internal channel 152); and the data sampling rate associated with the output electrodes 134a-134j. These values associated with the test device input data 214 may be permanently coupled to the test housing 130. The test device input data 214 may comprise a unique series of alpha-numeric values that are associated with that particular test housing 130 for use with the test system 100, which are received as input through the human-machine interface 116. In other embodiments, the test device input data 214 of the test housing 130 may comprise a scannable code, including, but not limited to a bar code, QR code, etc., and the test device input data 214 may be received as input by an optical scanning device coupled to and in communication with the controller 114 and processed by the controller 114 to determine the test device input data 214.

The set rate input data 216 is a pre-defined basal rate for the fluid that is to be dispensed from the fluid infusion device 102 during a basal test, which may be received as input when a basal test is selected to be performed. The basal rate is defined as a volume of fluid per unit time. The bolus delivery data 217 is optional input received from the user via the user's manipulation of the input device 108 that indicates that the bolus has been delivered by the fluid infusion device 102. The fluid quantity input data 218 is an expected or pre-defined volume of fluid to be received into the test housing 130 a pre-defined number of times, which may be received as input during a calibration test or a bolus test. In this regard, for a calibration test, pre-defined volumes of fluid may be dispensed into the test housing 130 through the infusion set inlet port 166 a predetermined number of times until the outlet port 160 of the internal channel 152 is reached. In one example, a calibrated, high-precision syringe pump may provide the known or pre-defined volume of fluid for delivery into the test housing 130 during a calibration test.

In a bolus test, a predetermined number of expected volumes of fluid or boluses are to be dispensed into the test housing 130 by the fluid infusion device 102. Generally, a bolus test determines an accuracy of the fluid infusion device 102 to dispense a number of discrete volumes or boluses of fluid, and the fluid quantity input data 218 is a pre-defined number of the discrete volumes to be dispensed into the test housing 130 along with a pre-defined expected volume to be received from the fluid infusion device 102. The end test data 219 is input received from the user via the user's manipulation of the input device 108 to end a basal test.

The UI control module 202 receives and processes the test type input data 212 and determines whether input has been received to select a bolus test, basal test or calibration test. Based on a received selection of a bolus test, the UI control module 202 sets bolus test command 220 for the test control module 208. The bolus test command 220 instructs the test control module 208 to begin a bolus test. Based on a received selection of a basal test, the UI control module 202 sets basal test command 222 for the test control module 208. The basal test command 222 instructs the test control module 208 to begin a basal test. Based on a received selection of a calibration test, the UI control module 202 sets calibration test command 224 for the calibration control module 206. The calibration test command 224 instructs the calibration control module 206 to begin a calibration test.

The UI control module 202 receives and processes the test device input data 214. Based on the test device input data 214, the UI control module 202 sets test device data 226 for the calibration control module 206 and the test control module 208. The test device data 226 is the unique identifier associated with the test housing 130, the distance D between each of the input electrodes 132a-132j and each of the output electrodes 134a-134j, respectively, of the test housing 130, the radius $R_c$ of the cross-sectional area of the internal channel 152 or $A_c$ the cross-sectional area of the internal channel 152, the thickness of the input electrodes 132a-132j, the manufacturing tolerance associated with the spacing between each of the input electrodes 132a-132j and each of the output electrodes 134a-134j, respectively, the manufacturing tolerance associated with the radius $R_c$ of the cross-sectional area of the internal channel 152 or a manufacturing tolerance associated with the cross-sectional area $A_c$ of the internal channel 152 (such as a manufacturing tolerance associated with a height and a width of the internal channel 152), and the data sampling rate associated with the output electrodes 134a-134j.

The UI control module 202 receives and processes the set rate input data 216. Based on the set rate input data 216, the UI control module 202 sets rate data 228 for the test control module 208. The rate data 228 is the pre-defined basal rate for the fluid infusion device 102. The UI control module 202 receives and processes the fluid quantity input data 218. Based on the fluid quantity input data 218, the UI control module 202 sets test fluid quantity data 230 for the calibration control module 206 and the test control module 208. The test fluid quantity data 230 is the pre-defined volume of fluid to be received into the test housing 130 each of the pre-defined number of times. The UI control module 202 receives and processes the bolus delivery data 217. Based on the bolus delivery data 217, the UI control module 202 sets bolus delivered command 261 for the test control module 208. The UI control module 202 receives and processes the end test data 219. Based on the end test data 219, the UI control module 202 sets end test command 263 for the test control module 208.

The UI control module 202 also receives as input bolus amount data 232 from the test control module 208. The bolus amount data 232 is a volume of fluid received from the fluid infusion device 102 at each of the pre-defined number of times over a period of time. Based on the bolus amount data 232, the UI control module 202 generates a bolus or bolus amount user interface (UI) 234 for display on the display 110 of the human-machine interface 116 (FIG. 1). The bolus amount user interface 234 graphically and/or textually displays the volume of fluid received from the fluid infusion device 102 at each of the pre-defined number of times over the period of time.

Figure 6:
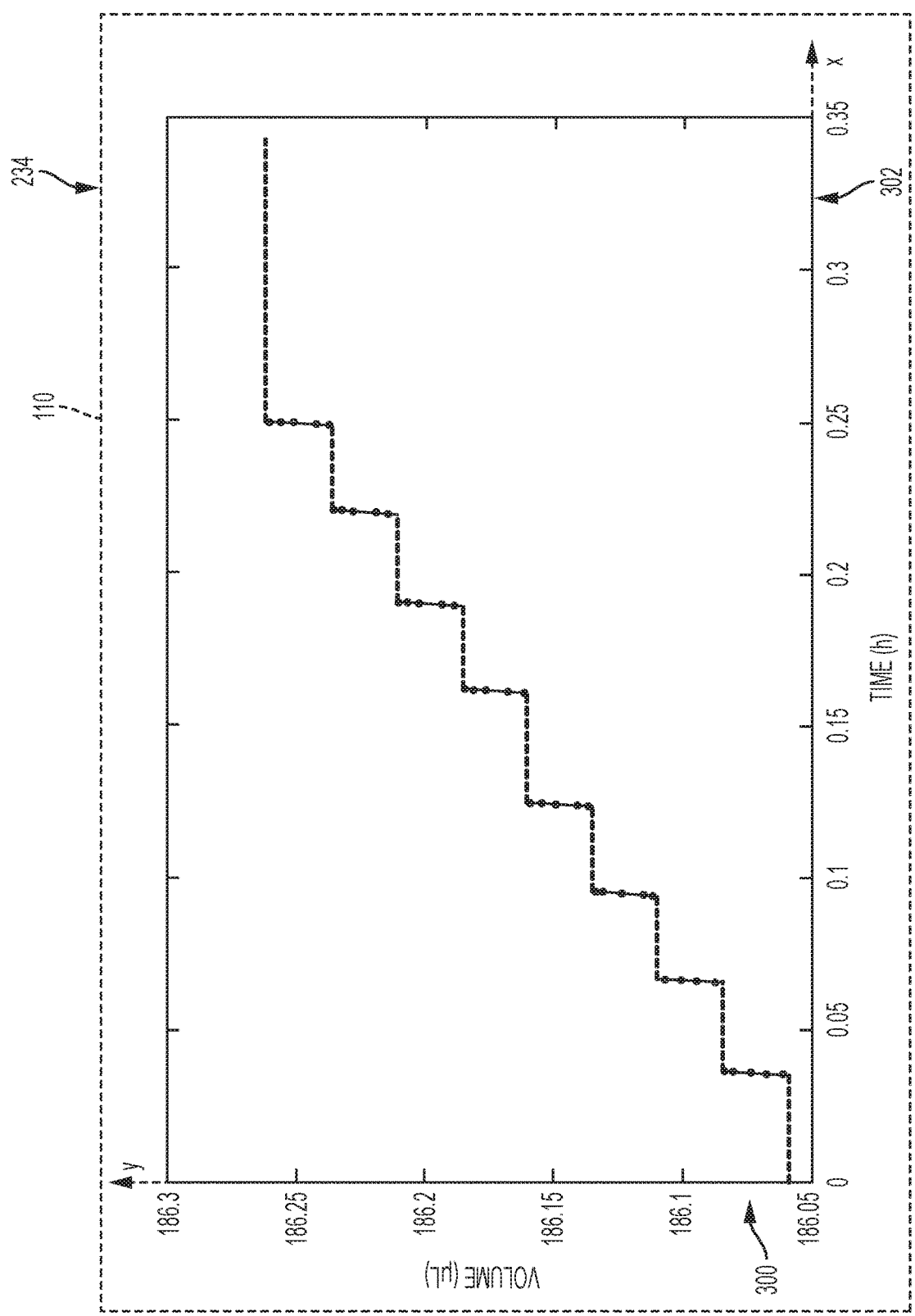
FIG. 6 illustrates an exemplary bolus or bolus amount user interface rendered by the test system on a display of a human-machine interface associated with the test system of FIG. 1, in accordance with various embodiments.

In one example, with reference to FIG. 6, an exemplary bolus amount user interface 234 is shown. In this example, the bolus amount user interface 234 is a graph, in which "Volume" in microliters (μL) is measured along a y-axis 300, and "Time" in hours (h) is measured on an x-axis 302. In one example, the y-axis 300 ranges from about 186.0 μL to about 186.3 μL, however, the y-axis 300 may have any desired range. The x-axis 302 ranges from 0 to 0.35 hours, however, the x-axis 302 may have any desired range. A graphical indicator 304, for example, a line, is associated with each discrete volume of fluid received by the test housing 130. As each volume of fluid received by the test housing 130 is discrete during a bolus test, the resultant graph has a plurality of steps or levels, with each step or level denoting a volume of fluid or bolus dispensed for a particular time frame. The steps or levels may be interconnected, as shown, if desired.

With reference back to FIGS. 4A and 4B, the UI control module 202 also receives as input bolus error data 236 from the test control module 208. The bolus error data 236 is an error calculated by the test control module 208 for each bolus received from the fluid infusion device 102. Stated another way, as will be discussed, the bolus error data 236 is a value of a difference between the test fluid quantity data 230 and the fluid received from the fluid infusion device 102 at each of the pre-defined number of times, which indicates a fluid delivery accuracy of the fluid infusion device 102.

Based on the bolus error data 236, the UI control module 202 generates a bolus error user interface (UI) 238 for display on the display 110 of the human-machine interface 116 (FIG. 1). The bolus error user interface 238 graphically and/or textually displays the error associated with each volume of fluid received from the fluid infusion device 102 at each of the pre-defined number of times.

Figure 7:
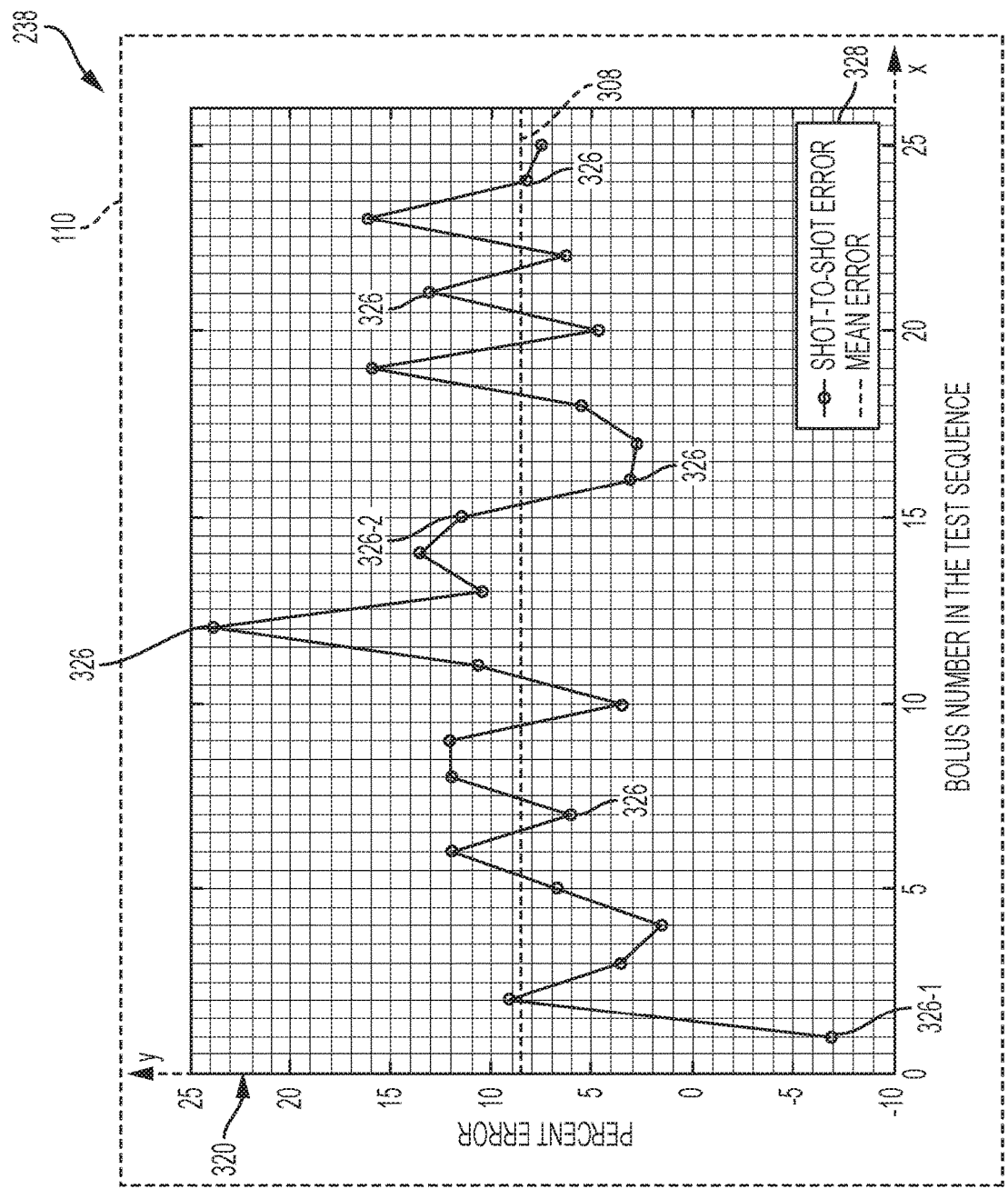
FIG. 7 illustrates an exemplary bolus error user interface rendered by the test system on the display of the human-machine interface associated with the test system of FIG. 1, in accordance with various embodiments.

In one example, with reference to FIG. 7, an exemplary bolus error user interface 238 is shown. In this example, the bolus error user interface 238 is a graph, in which "Percent Error" is measured along a y-axis 320, and "Bolus Number in the Test Sequence" is measured on an x-axis 322. In one example, the y-axis 320 ranges from −10 to 25, however, the y-axis 320 may have any desired range. The x-axis 322 ranges from 0 to 25, however, the x-axis 322 may have any desired range. A graphical indicator 326, for example, a circle, is associated with each number of fluid volumes received and is positioned at the error calculated for that particular received volume of fluid. For example, graphical indicator 326-1 is associated with the second volume of fluid received in the test housing 130, and has a percent error of about −6.5%; graphical indicator 326-2 is associated with the fifteenth volume of fluid received in the test housing 130, and has a percent error of about 11.6%. Each of the graphical indicators 326 may be interconnected with a line, which graphically illustrates the error between each bolus dispensed by the fluid infusion device 102. The bolus error user interface 238 also includes a mean bolus error may be graphically indicated on the bolus error user interface 238 as a dashed line 308. The mean bolus error may be calculated by the test control module 208 as an average of the errors calculated by the test control module 208 for each bolus received from the fluid infusion device 102. The bolus error user interface 238 may also include a key 328, which may be superimposed over a portion of the bolus error user interface 238. In various embodiments, the bolus error user interface 238 may also include a serial number of the fluid infusion device 102, which may be received as input to the UI control module 202 based on a user's interaction with the input device 108; a date; a time; a number of boluses delivered (from the bolus amount data 232); a size or volume of each of the boluses (from the test fluid quantity data 230); and the unique identifier of the test housing 130 from the test device input data 214.

With reference back to FIGS. 4A and 4B, the UI control module 202 also receives as input basal rate data 240 from the test control module 208. The basal rate data 240 is a volume of fluid delivered by the fluid infusion device 102 over a period of time. Based on the basal rate data 240, the UI control module 202 generates a basal rate user interface (UI) 242 for display on the display 110 of the human-machine interface 116 (FIG. 1). The basal rate user interface 242 graphically and/or textually displays the volume of fluid delivered by the fluid infusion device 102 over the period of time.

Figure 8:
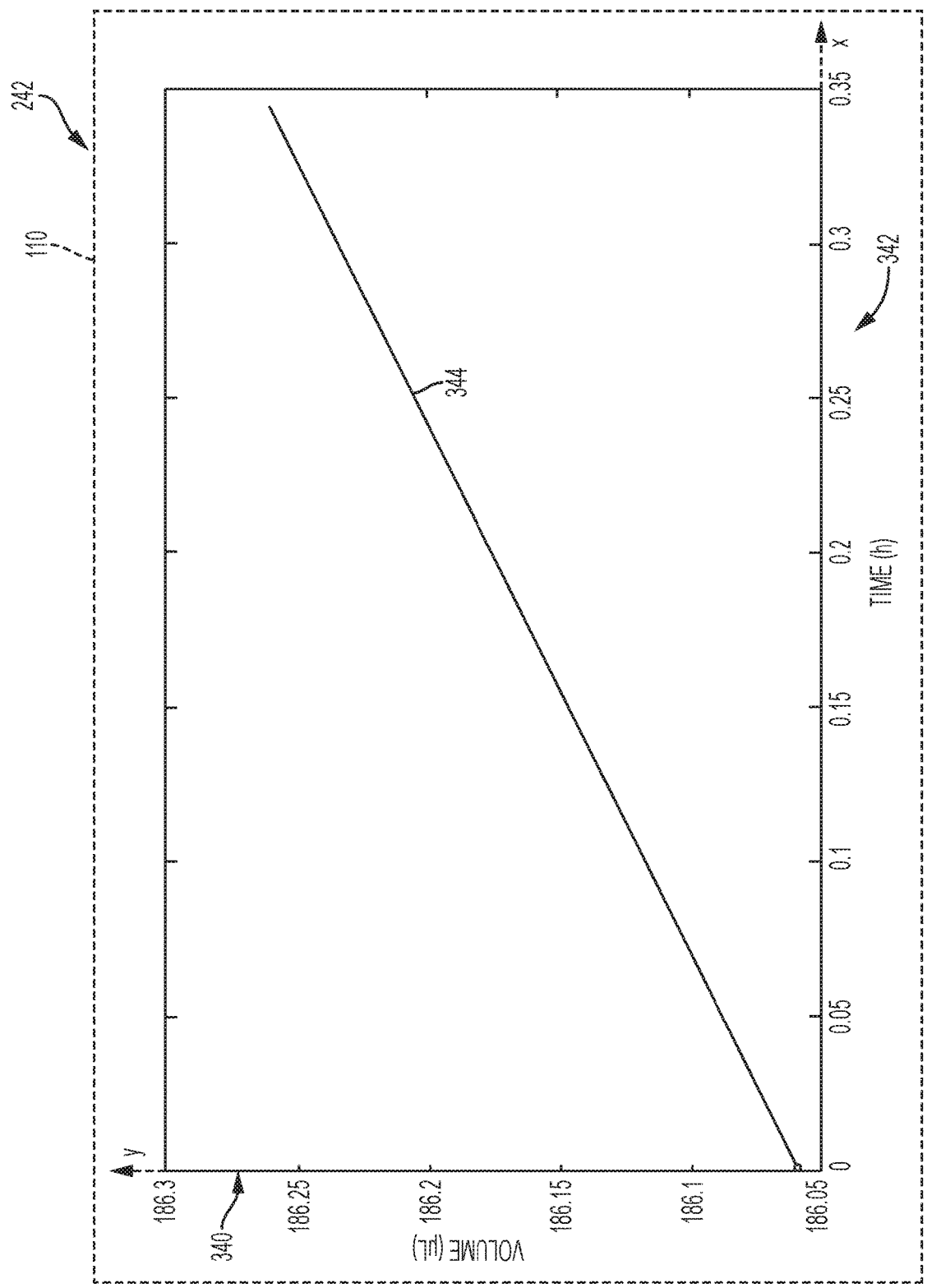
FIG. 8 illustrates an exemplary basal rate user interface rendered by the test system on the display of the human-machine interface associated with the test system of FIG. 1, in accordance with various embodiments.

In one example, with reference to FIG. 8, an exemplary basal rate user interface 242 is shown. In this example, the basal rate user interface 242 is a graph, in which "Volume" in microliters (μL) is measured along a y-axis 340, and "Time" in hours (h) is measured on an x-axis 342. In one example, the y-axis 340 ranges from about 186.0 μL to about 186.3 μL, however, the y-axis 340 may have any desired range. The x-axis 342 ranges from 0 to 0.35 hours, however, the x-axis 342 may have any desired range. A graphical indicator 344, for example, a line, is used to illustrate the amount of fluid delivered by the fluid infusion device 102 over the period of time.

With reference back to FIGS. 4A and 4B, the UI control module 202 also receives as input basal error data 244 from the test control module 208. The basal error data 244 is an error calculated by the test control module 208 for the basal rate received from the fluid infusion device 102, and generally includes a maximum error value, minimum error value and an overall error value for the dispensing of the fluid by the fluid infusion device 102 over the period of time. Stated another way, as will be discussed, the basal error data 244 is a maximum value, a minimum value and an overall value of a difference between the rate data 228 and the rate of fluid received from the fluid infusion device 102 over the period of time, which indicates a fluid delivery accuracy of the fluid infusion device 102. Based on the basal error data 244, the UI control module 202 generates a basal error user interface (UI) 246 for display on the display 110 of the human-machine interface 116 (FIG. 1). The basal error user interface 246 graphically and/or textually displays the error associated with the amount of fluid received from the fluid infusion device 102 over the period of time.

Figure 9:
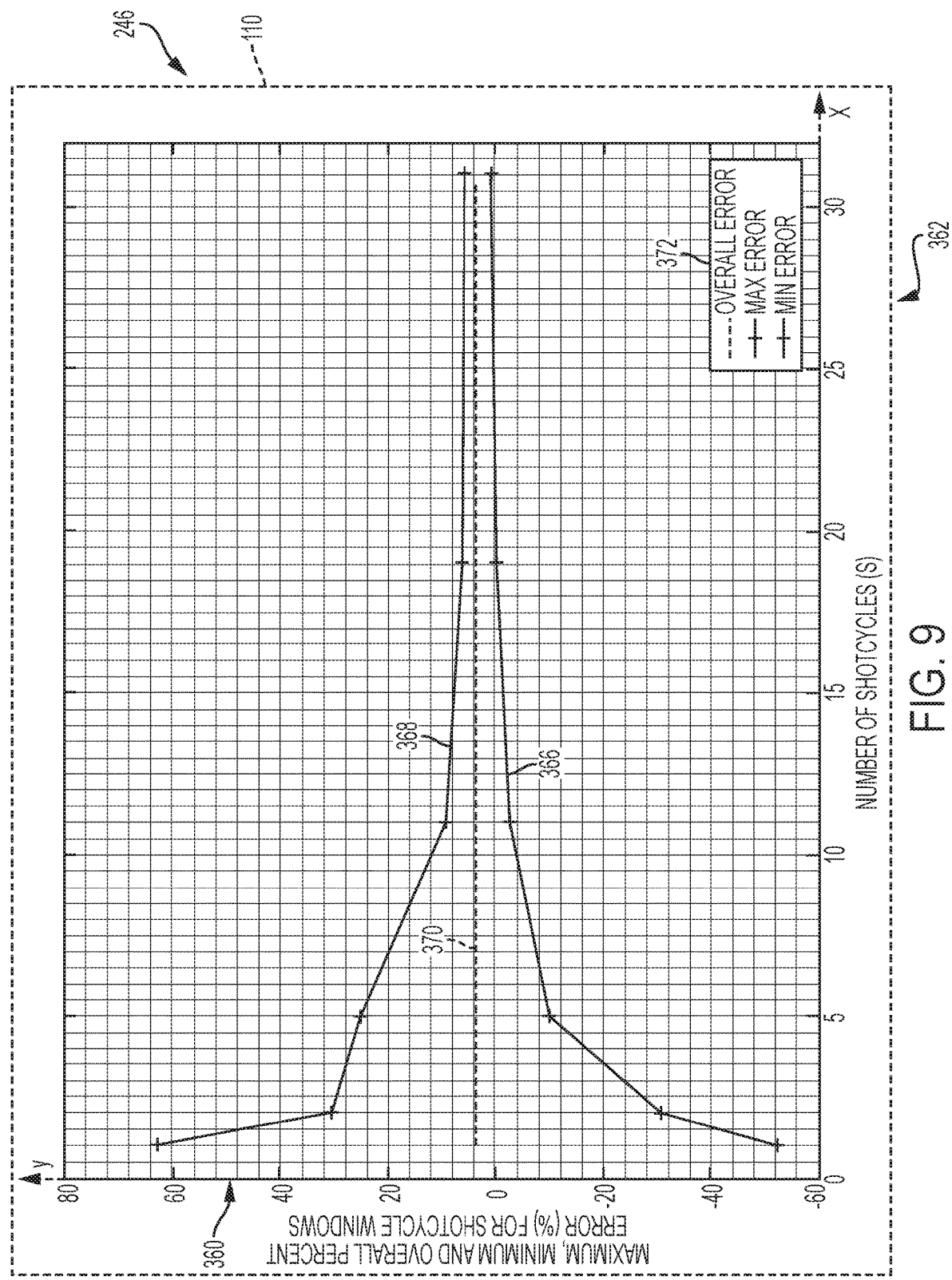
FIG. 9 illustrates an exemplary basal error user interface rendered by the test system on the display of the human-machine interface associated with the test system of FIG. 1, in accordance with various embodiments.

In one example, with reference to FIG. 9, an exemplary basal error user interface 246 is shown. In this example, the basal error user interface 246 is a graph, in which "Maximum, Minimum, and Overall Percent Error for Shotcycle Windows" is measured in percent (%) along a y-axis 360, and "Number of Shotcycles" is measured on an x-axis 362. Generally, the fluid infusion device 102 delivers fluid at data points, increments or shotcycles over the pre-defined period of time. In one example, the y-axis 360 ranges from −60 to 80, however, the y-axis 360 may have any desired range. The x-axis 362 ranges from 0 to 30, however, the x-axis 362 may have any desired range. A first graphical indicator 366, for example, a line with a plurality of raised crosses, graphically indicates a minimum error for the fluid infusion device 102 over the number of shotcycles. A second graphical indicator 368, for example, a line with a plurality of in-line crosses, graphically indicates a maximum error for the fluid infusion device 102 over the number of shotcycles. A third graphical indicator 370, for example, a dashed line, graphically indicates an overall error for the fluid infusion device 102 over the number of shotcycles. The basal error user interface 246 may also include a key 372, which may be superimposed over a portion of the basal error user interface 246. In various embodiments, the basal error user interface 246 may also include a serial number of the fluid infusion device 102, which may be received as input to the UI control module 202 based on a user's interaction with the input device 108; a date; a time; a basal rate (from the rate data 228); and the unique identifier of the test housing 130 from the test device input data 214.

With reference back to FIGS. 4A and 4B, the UI control module 202 also receives as input bolus activation data 248 from the test control module 208. The bolus activation data 248 is data that associates the activation of each of the output electrodes 134a-134j with a particular time and a particular volume of fluid received from the fluid infusion device 102. Stated another way, the bolus activation data 248 identifies which one of the output electrodes 134a-134j is activated at a particular time by a particular one of the volumes or boluses of fluid. Based on the bolus activation data 248, the UI control module 202 generates a bolus activation user interface (UI) 250 for display on the display 110 of the human-machine interface 116 (FIG. 1). The bolus activation user interface 250 graphically and/or textually displays the volume of fluid received from the fluid infusion device 102 over the period of time.

With to FIGS. 4A and 4B, the UI control module 202 also receives as input basal activation data 252 from the test control module 208. The basal activation data 252 is data that associates the activation of each of the output electrodes 134a-134j with a particular time and a particular shotcycle of fluid received from the fluid infusion device 102. Stated another way, the basal activation data 252 identifies which one of the output electrodes 134a-134j is activated at a particular time by a particular shotcycle of the fluid delivered by the fluid infusion device 102. Based on the basal activation data 252, the UI control module 202 generates a basal activation user interface (UI) 254 for display on the display 110 of the human-machine interface 116 (FIG. 1). The basal activation user interface 254 graphically and/or textually displays the volume of fluid delivered by the fluid infusion device 102 over the period of time.

Based on at least one of the bolus activation data 248 and the basal activation data 252, the UI control module 202 also outputs data log 256. The data log 256 is a text file, for example, which includes the bolus activation data 248, the basal activation data 252 or test device calibration data 260 in a list form. The data log 256 may also include other characteristics associated with a bolus test or basal test performed by the test system 100, including, but not limited to: a date; a type of test (from the test type input data 212); a unique identifier of the test housing 130 (from the test device input data 214); a calibration profile associated with the test housing 130 that was used for the determination of the amount of fluid dispensed by the fluid infusion device 102 (from calibration data 258); a type of electrolyte (which may be received from the user through the input device 108 and stored in the media 182); a concentration of the electrolyte (which may be received from the user through the input device 108 and stored in the media 182); settings for the voltage applied to the input electrodes 132a-132j (which may be received from the user through the input device 108 and stored in the media 182); a test number (which may be received from the user through the input device 108 and stored in the media 182); a protocol number (which may be received from the user through the input device 108 and stored in the media 182); a type of fluid infusion device 102 (which may be received from the user through the input device 108 and stored in the media 182); a serial number of the fluid infusion device 102 (which may be received from the user through the input device 108 and stored in the media 182); a type of infusion set 104 used with the fluid infusion device 102 (which may be received from the user through the input device 108 and stored in the media 182); a lot number of the infusion set 104 (which may be received from the user through the input device 108 and stored in the media 182); a type of test (from the test type input data 212); a volume of fluid expected for each fluid delivery (from the fluid quantity input data 218); a delivery frequency (which may be received from the user through the input device 108 and stored in the media 182); a total delivery amount (from the fluid quantity input data 218); a sample rate for the output electrodes 134a-134j (which may be received from the user through the input device 108 and stored in the media 182); and notes from the user (which may be received from the user through the input device 108 and stored in the media 182).

The data log 256 may also include other characteristics associated with a calibration test performed by the test system 100, including, but not limited to: a date; a unique identifier of the test housing 130 (from the test device input data 214); a length of the internal channel 152 of the test housing 130 (which may be received from the user through the input device 108 and stored in the media 182); a height of the internal channel 152 of the test housing 130 (which may be received from the user through the input device 108 and stored in the media 182); a width of the internal channel 152 of the test housing 130 (which may be received from the user through the input device 108 and stored in the media 182); a spacing of the input electrodes 132a-132j and/or the output electrodes 134a-134j (which may be received from the user through the input device 108 and stored in the media 182); a type of electrolyte (which may be received from the user through the input device 108 and stored in the media 182); a concentration of the electrolyte (which may be received from the user through the input device 108 and stored in the media 182); and settings for the voltage applied to the input electrodes 132a-132j (which may be received from the user through the input device 108 and stored in the media 182). Generally, the settings for the voltage applied to the input electrodes 132a-132j are pre-defined, based on the type of power source 112 employed with the test system 100 (FIG. 1).

The UI control module 202 also receives as input bolus prompt 255 from the test control module 208. The bolus prompt 255 is a command to prompt the user to deliver another volume of fluid or a bolus to the test housing 130 (FIG. 1). Based on the receipt of the bolus prompt 255, the UI control module 202 outputs a prompt user interface (UI) 257. The prompt user interface 257 may be a graphical and/or textual notification, which may be superimposed over a portion of a user interface on the display 110, which instructs the user to dispense another volume of fluid or a bolus into the test housing 130 (FIG. 1). For example, the prompt user interface 257 may comprise a pop-up window, which states "Deliver Bolus" or the like.

The UI control module 202 also receives as input error flag 259 from the test control module 208. The error flag 259 is a notification that a communication error exists between the test housing 130 and the controller 114. For example, the error flag 259 indicates that one or more of the input electrodes 132a-132j and/or output electrodes 134a-134j are uncoupled from or no longer in communication with the controller 114. Based on the error flag 259, the UI control module 202 outputs an error user interface (UI) 265. The error user interface 265 may be a graphical and/or textual notification, which may be superimposed over a portion of a user interface on the display 110, which instructs the user that a communication error exists. For example, the error user interface 265 may comprise a pop-up window, which states "Check Electrodes" or the like.

The calibration datastore 204 stores data in the form of a calibration table that correlates the unique identifier of the test housing 130 with calibration data 258 for the particular test housing 130. Thus, the calibration datastore 204 stores one or more lookup tables, which provide calibration data 258 that corresponds with unique identifier of the test housing 130 received from the test device data 226. In one example, the calibration data 258 stored in the calibration datastore 204 is populated based on the test device calibration data 268 by the calibration control module 206 during a calibration test. It should be noted, however, that the calibration data 258 stored in the calibration datastore 204 may be pre-defined, or default values.

The calibration control module 206 receives as input the calibration test command 224 from the UI control module 202. Based on the receipt of the calibration test command 224, the calibration control module 206 receives as input the test fluid quantity data 230 and the test device data 226 from the UI control module 202. The calibration control module 206 sets a counter equal to zero. The calibration control module 206 outputs voltage data 262. The voltage data 262 is one or more control signals to the power source 112 to alternate and apply the voltage to the respective input electrodes 132a-132j. Based on the output of the voltage data 262, the calibration control module 206 receives as input activation data 264. The activation data 264 is the signal received from the respective one of the output electrodes 134a-134j based on the voltage potential created by the voltage applied to the respective input electrode 132a-132j that when the fluid 118 is present causes the current to pass through the fluid 118 within the internal channel 152 (FIG. 3) to the respective output electrode 134a-134j. In one example, the calibration control module 206 determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118. The calibration control module 206 also determines, based on the activation data 264, which of the output electrodes 134a-134j is activated by the fluid 118 flowing within the internal channel 152

(FIG. 3). Based on the current increment of the counter, the calibration control module 206 determines which pre-defined volume of fluid was received into the test housing 130 based on the test fluid quantity data 230. In this regard, as the test fluid quantity data 230 generally includes an ordered listing of the pre-defined volumes of fluid to be received into the test housing 130, the calibration control module 206 determines which pre-defined volume of fluid was received based on the count of the counter.

The calibration control module 206 associates the identified pre-defined volume of fluid received into the test housing 130 with the respective one or more of the activated output electrode 134a-134j for the particular test housing 130 identified in the test device data 226, and stores this data as test device calibration data 268 in the calibration datastore 204. The calibration control module 206 determines whether each of the output electrodes 134a-134j has been activated. The calibration control module 206 repeats this process until each of the output electrodes 134a-134j has been activated. If each of the output electrodes 134a-134j has been activated, the calibration control module 206 outputs stop voltage command 270. The stop voltage command 270 is one or more control signals to the power source 112 to stop the application of the voltage to the input electrodes 132a-132j. The calibration control module 206 also sets the test device calibration data 268 for the UI control module 202. Generally, the test device calibration data 268 indicates a known volume of fluid to activate each output electrode 134a-134j in the internal channel 152 over an entire length of the internal channel 152.

For example, a delivery amount of 250 nanolitres (nL) is designed to cover or activate 10 output electrodes 134a-134j. While delivering the calibrated amount of 250 nanolitres (nL) during an exemplary calibration test, nine output electrodes 134a-134j are determined to be activated. The calibration control module 206 determines that nine output electrodes 134a-134j are activated per 250 nanolitres (nL) and sets this as the test device calibration data 268.

With reference to FIG. 5, a dataflow diagram illustrates various embodiments of the test control module 208 of the test control system 200, which may be embedded within the controller 114. Various embodiments of the test control module 208 according to the present disclosure can include any number of sub-modules embedded within the controller 114. As can be appreciated, the sub-modules shown in FIG. 5 may be combined and/or further partitioned to similarly control the input electrodes 132a-132j and determine an amount of fluid dispensed by the fluid infusion device 102 based on the activated output electrode 134a-134j. In various embodiments, the test control module 208 includes a test device manager module 400, an electrode control module 402, a bolus datastore 404, a bolus monitor module 406, a basal datastore 408 and a basal monitor module 410.

The test device manager module 400 receives as input test device data 226 from the UI control module 202 (FIGS. 4A and 4B). Based on the test device data 226, the test device manager module 400 queries the calibration datastore 204 (FIGS. 4A and 4B), and retrieves the calibration data 258 associated with the unique identifier of the test housing 130 (from the test device data 226). The test device manager module 400 sets the test device data 226 and the calibration data 258 as housing data 412 for the bolus monitor module 406 and the basal monitor module 410. The housing data 412 includes the calibration data 258 associated with the identified test housing 130, along with the distance D between each of the input electrodes 132a-132j and each of the output electrodes 134a-134j, respectively, of the test housing 130, the radius $R_c$ of the cross-sectional area of the internal channel 152 or the cross-sectional area $A_c$ of the internal channel 152, the thickness of the input electrodes 132a-132j, the manufacturing tolerance associated with the spacing between each of the input electrodes 132a-132j and each of the output electrodes 134a-134j, respectively, the manufacturing tolerance associated with the radius $R_c$ of the cross-sectional area of the internal channel 152 or a manufacturing tolerance associated with the cross-sectional area of the internal channel 152 (such as a manufacturing tolerance associated with a height and a width of the internal channel 152), and the data sampling rate associated with the output electrodes 134a-134j.

The electrode control module 402 receives as input a start command 414 from the bolus monitor module 406 or the basal monitor module 410. The start command 414 is an instruction to apply a voltage to the input electrodes 132a-132j. Based on the start command 414, the electrode control module 402 outputs the voltage data 262 to the power source 112. The electrode control module 402 also receives as input a stop command 416 from the bolus monitor module 406 or the basal monitor module 410. The stop command 416 is an instruction to stop applying a voltage to the input electrodes 132a-132j. Based on the stop command 416, the electrode control module 402 outputs the stop voltage command 270 to the power source 112.

The bolus datastore 404 stores the bolus activation data 248 associated with a bolus test. Thus, the bolus datastore 404 stores one or more tables, which provide the bolus activation data 248 that corresponds with a particular discrete volume of fluid or bolus dispensed into the test housing 130. In one example, the bolus activation data 248 stored in the bolus datastore 404 is populated by the bolus monitor module 406 during a bolus test.

The bolus monitor module 406 receives as input the bolus test command 220 from the UI control module 202. Based on the receipt of the bolus test command 220, the bolus monitor module 406 sets the start command 414 for the electrode control module 402, and sets a value of a counter as equal to one. In one example, the bolus monitor module 406 may also set the bolus prompt 255 for the UI control module 202 to instruct the user to dispense the bolus into the test housing 130, and may determine if the bolus delivered command 261 has been received from the UI control module 202. The bolus monitor module 406 receives as input the activation data 264. In one example, the bolus monitor module 406 determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118.

The bolus monitor module 406 also receives as input time data 266 and the test fluid quantity data 230. The time data 266 is a current time, which may be received from other modules associated with the test control module 208, such as an internal clock associated with the processor 180. The bolus monitor module 406 also determines, based on the activation data 264 and the time data 266, which of the output electrodes 134a-134j have been activated by the fluid 118 received into the internal channel 152 and at what time. Based on the current increment of the counter and the test fluid quantity data 230, the bolus monitor module 406 determines which volume of fluid was received into the test housing 130. The bolus monitor module 406 associates the delivery of the fluid with the activated output electrodes 134a-134j, and stores this as the bolus activation data 248 in the bolus datastore 404. The bolus monitor module 406 also sets the bolus activation data 248 for the UI control module 202 (FIGS. 4A and 4B).

The bolus monitor module 406 also receives as input the housing data 412. Based on the housing data 412 and the activation data 264, the bolus monitor module 406 determines the bolus amount data 232. In one example, the bolus monitor module 406 uses the following equation to determine the volume of fluid received from the fluid infusion device 102 for the bolus:

$$(A_c \pm x_1)((D \pm x_2) + W_e) = V \qquad (2)$$

Wherein, $A_c$ is the cross-sectional area of the internal channel 152 in millimeters (mm); $x_1$ is the manufacturing tolerance associated with the cross-sectional area of the internal channel 152, which in one example, is a manufacturing tolerance associated with the width and the height of the internal channel 152 (in the example of a cylindrical internal channel 152, $x_1$ is the manufacturing tolerance associated with the radius ($R_c$) of the internal channel 152); D is the distance between each of the input electrodes 132a-132j and each of output electrodes 134a-134j, respectively, of the test housing 130 (measured between respective ends 174a-174j; 176a-176j, which in this example is the same) in millimeters (mm); $x_2$ is the manufacturing tolerance associated with the spacing between each of the input electrodes 132a-132j and each of the output electrodes 134a-134j, respectively; $W_e$ is the thickness of the input electrodes 132a-132j and the output electrodes 134a-134j in millimeters (mm); and V is the discrete volume of fluid observed by the output electrode 134a-134j in cubic millimeters (mm$^3$). In this example, $A_c$, D, $x_1$, $x_2$ and $W_e$ are all pre-determined or pre-defined known values that are received as housing data 412. In one example, the $A_c$ is the cross-sectional area of the internal channel 152 and in this example, $A_c = \pi(R_c)^2$, wherein $R_c$ is the pre-defined known value of the radius of the internal channel 152. In this example, $A_c$ of the internal channel 152 may be calculated by the processor 180 based on the known value of $R_c$, which is received in the housing data 412. By having current pass through a given output electrode 134a-134j, the bolus monitor module 406 determines how far the fluid 118 has traveled and, based on equation (2) and the calibration data 258, calculates how much volume of fluid has been delivered. In this regard, based on the calibration data 258 retrieved with the housing data 412, the bolus monitor module 406 compares the determined volume V of fluid from equation (2) with the calibration data 258 and determines the volume of fluid delivered. Referencing the prior example, if nine output electrodes 134a-134j have been activated, the bolus monitor module 406 determines that 250 nanolitres (nL) has been delivered. The bolus monitor module 406 associates the volume of fluid delivered with the particular pre-defined volume of fluid or bolus received (based on the count of the counter) as the bolus amount data 232 for the UI control module 202 (FIGS. 4A and 4B).

Based on the bolus amount data 232 and the test fluid quantity data 230, the bolus monitor module 406 determines the bolus error data 236. In one example, the bolus monitor module 406 divides the determined volume of fluid delivered with the expected volume of fluid received as input in the test fluid quantity data 230 and multiplies the value by 100 to arrive at a percent error for the particular bolus received from the fluid infusion device 102. The bolus monitor module 406 sets the bolus error data 236 for the UI control module 202 (FIGS. 4A and 4B).

After determining the volume of fluid delivered, the bolus monitor module 406 increments the counter by one. The bolus monitor module 406 determines whether the counter is greater than a pre-defined threshold count. In one example, the pre-defined threshold count is about 25. If the counter is less than the pre-defined threshold count, the bolus monitor module 406 sets bolus prompt 255 for the UI control module 202.

Once the bolus monitor module 406 ceases to receive activation data 264 such that the output electrodes 134a-134j are no longer being activated, the bolus monitor module 406 sets the stop command 416 for the electrode control module 402. The bolus monitor module 406 may also set the error flag 259 for the UI control module 202 based on activation data 264 not being received from one or more of the output electrodes 134a-134j.

The basal datastore 408 stores the basal activation data 252 associated with a basal test. Thus, the basal datastore 408 stores one or more tables, which provide the basal activation data 252 that corresponds with a particular volume of fluid received over a period of time or basal rate dispensed into the test housing 130. In one example, the basal activation data 252 stored in the basal datastore 408 is populated by the basal monitor module 410 during a basal test.

The basal monitor module 410 receives as input the basal test command 222 from the UI control module 202. Based on the receipt of the basal test command 222, the basal monitor module 410 sets the start command 414 for the electrode control module 402, and sets a value of a timer as equal to zero. The basal monitor module 410 receives as input the activation data 264. In one example, the basal monitor module 410 determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118.

The basal monitor module 410 also receives as input the time data 266 and the rate data 228. The basal monitor module 410 determines, based on the activation data 264 and the time data 266, which of the output electrodes 134a-134j have been activated by the fluid 118 received into the internal channel 152 and at what time by a particular shotcycle. Based on the current time of the timer, the basal monitor module 410 associates the delivery of the fluid 118 with the activated output electrodes 134a-134j, and stores this as the basal activation data 252 in the basal datastore 408. Generally, the particular shotcycle is determined based on the fluid infusion device 102 being employed with the test system 100 and the repeating patterns of discrete fluid deliveries the fluid infusion device 102 may employ or the smallest amount of time and volume that is desired to be evaluated for a given basal rate. The shotcycles associated with the particular fluid infusion device 102 and/or the smallest of amount of time and volume that is desired to be evaluated may be received as input data from the operator, or may be pre-defined and stored in the memory 182 associated with the processor 180. The basal monitor module 410 also sets the basal activation data 252 for the UI control module 202 (FIGS. 4A and 4B).

The basal monitor module 410 also receives as input the housing data 412. Based on the housing data 412 and the activation data 264, the basal monitor module 410 determines the basal rate data 240. In one example, the basal monitor module 410 uses equation (3), below, to determine the volume of fluid received from the fluid infusion device 102 over a period of time:

$$\frac{(A_c \pm x_1)((D \pm x_2) + W_e)}{t} = V_r \quad (3)$$

Wherein, $A_c$ is the cross-sectional area of the internal channel 152 in millimeters (mm); $x_1$ is the manufacturing tolerance associated with the cross-sectional area of the internal channel 152, which in one example, is a manufacturing tolerance associated with the width and the height of the internal channel 152 (in the example of a cylindrical internal channel 152, $x_1$ is the manufacturing tolerance associated with the radius ($R_c$) of the internal channel 152); D is the distance between each of the input electrodes 132a-132j and each of the output electrodes 134a-134j, respectively, of the test housing 130 (measured between respective ends 174a-174j; 176a-176j, which in this example is the same) in millimeters (mm); $x_2$ is the manufacturing tolerance associated with the spacing between each of the input electrodes 132a-132j and each of the output electrodes 134a-134j, respectively; $W_e$ is the thickness of the input electrodes 132a-132j and the output electrodes 134a-134j in millimeters (mm); t is the time of the timer (in seconds) and $V_r$ is the volume of fluid observed by the output electrode 134a-134j per the period of time measured by the timer in cubic millimeters per second (mm³/s). As discussed with regard to equation (2), $A_c$, D, $x_1$, $x_2$ and $W_e$ are all pre-determined or pre-defined known values. In one example, the $A_c$ is the cross-sectional area of the internal channel 152 and in this example, $A_c = \pi(R_c)^2$, wherein $R_c$ is the pre-defined known value of the radius of the internal channel 152. In this example, $A_c$ of the internal channel 152 may be calculated by the processor 180 based on the known value of $R_c$, which is received in the housing data 412.

By having current pass through a given output electrode 134a-134j, the basal monitor module 410 determines how far the fluid 118 has traveled and, based on equation (3) and the calibration data 258, calculates how much volume of fluid has been delivered per unit time. In this regard, based on the calibration data 258 retrieved with the housing data 412, the basal monitor module 410 compares the determined volume of fluid per period of time from equation (3) with the calibration data 258 and determines the volume of fluid delivered per period of time. The basal monitor module 410 sets the determined volume delivered per period of time as the basal rate data 240 for the UI control module 202 (FIGS. 4A and 4B).

Based on the basal rate data 240 and the rate data 228, the basal monitor module 410 determines the basal error data 244. In one example, the basal monitor module 410 determines the basal error data 235 based equation (4), below:

$$\text{Error}_i = \left( \frac{\frac{Vr_{i+\frac{P}{S}} - Vr_i}{t_{i+\frac{P}{S}} - t_i} - r}{r} \right) * 100\% \quad (4)$$

Wherein $Vr_i$ is the volume at a given data point (i) in cubic millimeters (mm³) as determined from equation (3); t is the time elapsed at the given data point as measured by the timer; P is one hour in seconds (s); S is the data sampling rate of the output electrodes 134a-134j, which is received from the housing data 412; r is the input basal rate or the rate data 228 in microliters per hour (μL/h); and $\text{Error}_i$ is the overall error value for the dispensing of the fluid by the fluid infusion device 102 over the period of time in percent (%). Generally, the basal rate data 240 calculates the $\text{Error}_i$ value for a plurality of data points over a basal test, and in one example, each data point equal to about one hour of the particular basal test for a 24 hour basal test. The basal monitor module 410 also determines the maximum error for the basal test, which is the largest calculated $\text{Error}_i$ value for the basal test. The basal monitor module 410 determines the minimum error for the basal test, which is the smallest calculated $\text{Error}_i$ value for the basal test. The basal monitor module 410 sets the $\text{Error}_i$ value determined for the data point, along with the maximum error and the minimum error as the basal rate data 240 for the UI control module 202 (FIGS. 4A and 4B).

After determining the volume of fluid delivered per time, the basal monitor module 410 determines whether each of the output electrodes 134a-134j has been activated in the internal channel 152 of the test housing 130. If true, the basal monitor module 410 sets the stop command 416 for the electrode control module 402. Otherwise, the basal monitor module 410 determines whether the end test command 263 has been received as input from the UI control module 202. If the end test command 263 has been received, the basal monitor module 410 sets the stop command 416. Otherwise, the basal monitor module 410 continues to monitor for the activation data 264.

Figure 10:
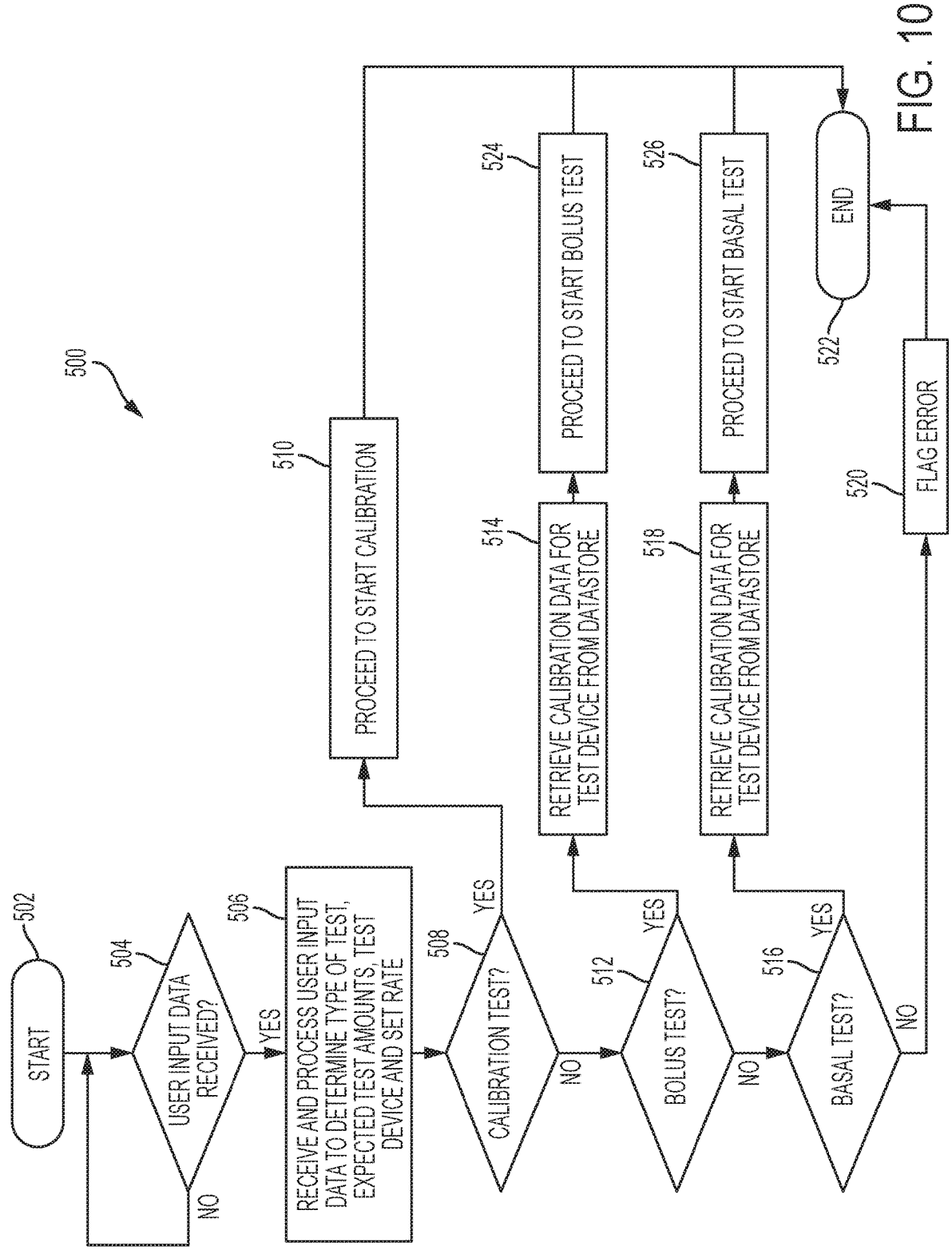
FIG. 10 is a flowchart illustrating a control method for the test system of FIG. 1, in accordance with various embodiments.

Referring now to FIG. 10, and with continued reference to FIGS. 1-5, a flowchart illustrates a control method 500 that can be performed by the test control system 200 of FIGS. 1-5 in accordance with the present disclosure. In various embodiments, the control method 500 is performed by the processor 180 of the controller 114. As can be appreciated in light of the disclosure, the order of operation within the method is not limited to the sequential execution as illustrated in FIG. 10, but may be performed in one or more varying orders as applicable and in accordance with the present disclosure. In various embodiments, the control method 500 can be scheduled to run based on one or more predetermined events, and/or can run continuously during operation of the test system 100.

The method begins at 502. At 504, the method determines whether input data 210 has been received from the user's manipulation of the input device 108. If input data 210 has been received, the method proceeds to 506. Otherwise, the method loops.

At 506, the method receives and processes the input data 210 to determine the type of test (test type input data 212), the expected pre-defined volumes of fluid that are to be received the particular number of times (fluid quantity input data 218), data associated with the particular test device (test device input data 214) and the set rate (set rate input data 216). At 508, the method determines whether the test type input data 212 is a calibration test. If true, the method proceeds to 510. Otherwise, at 512, the method determines whether the test type input data 212 is a bolus test. If true, the method proceeds to 514. Otherwise, at 516, the method determines whether the test type input data 212 is a basal test. If true, the method proceeds to 518. Otherwise, the method flags an error at 520 and ends at 522. Optionally, the method may loop from 516 to 504.

At 510, the method proceeds to start a calibration test, as will be discussed with regard to FIG. 11. With the determination of a bolus test, at 514, the method retrieves the calibration data 258 associated with the particular test device (based on the test device input data 214) and at 524, the method proceeds to start a bolus test, as will be discussed with regard to FIG. 12. With the determination of a basal test, at 518, the method retrieves the calibration data 258 associated with the particular test device (based on the test device input data 214) and at 526, the method proceeds to start a basal test, as will be discussed with regard to FIG. 13.

Figure 11:
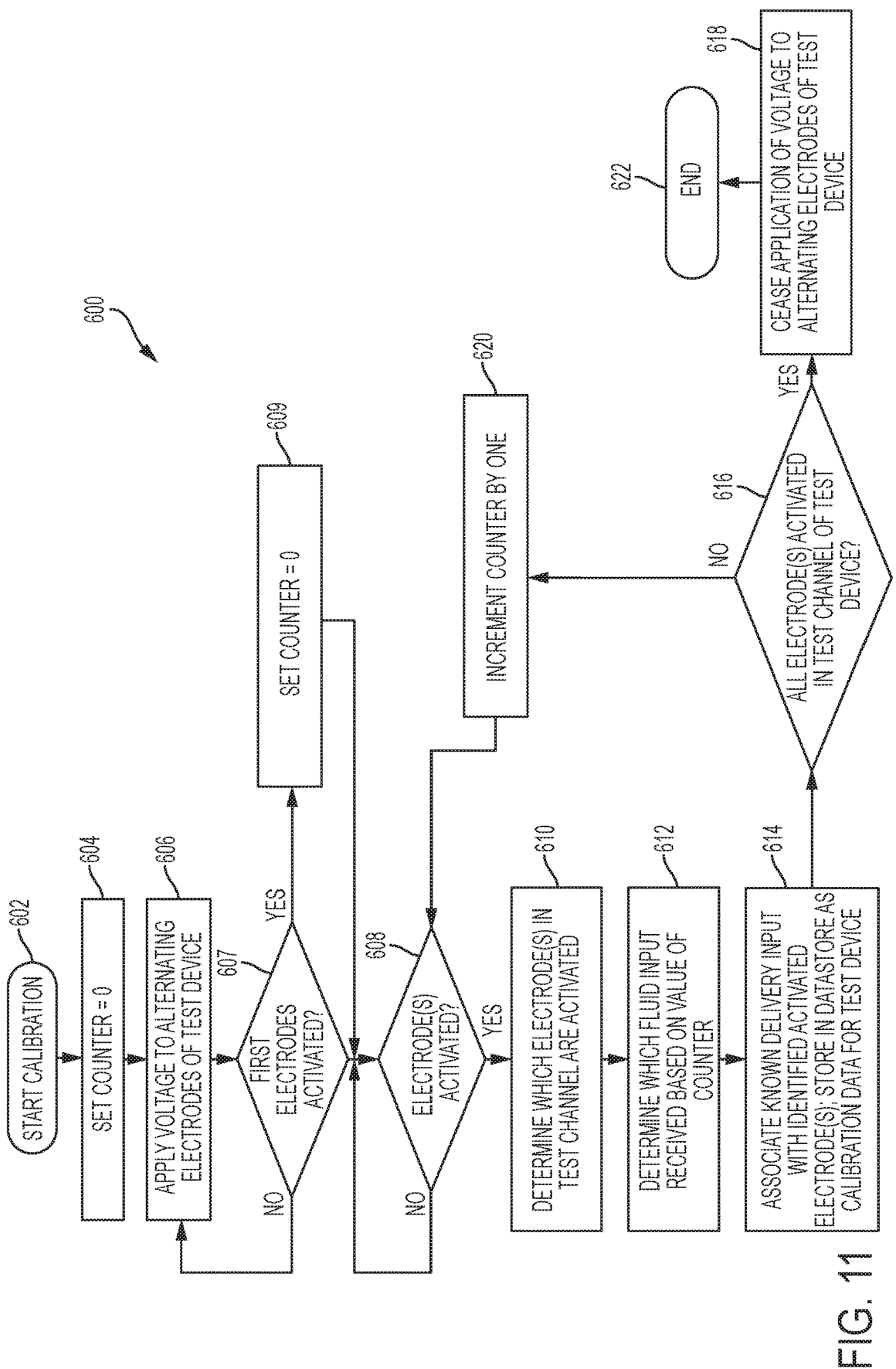
FIG. 11 is a flowchart illustrating a calibration control method for the test system of FIG. 1, in accordance with various embodiments.

Referring now to FIG. 11, and with continued reference to FIGS. 1-5, a flowchart illustrates a calibration method 600 that can be performed by the test control system 200 of FIGS. 1-5 in accordance with the present disclosure. In various embodiments, the calibration method 600 is performed by the processor 180 of the controller 114. As can be appreciated in light of the disclosure, the order of operation within the method is not limited to the sequential execution as illustrated in FIG. 11, but may be performed in one or more varying orders as applicable and in accordance with the present disclosure. In various embodiments, the calibration method 600 can be scheduled to run based on one or more predetermined events, such as based on the receipt of the input data 210. Prior to beginning the calibration method, the operator inputs commands to a user interface of the fluid infusion device 102 to prime the fluid infusion device 102 and the test housing 130.

The method begins at 602. At 606, the method commands the power source 112 to apply a voltage to alternating ones of the input electrodes 132a-132j of the fluid delivery test device 106 or outputs the voltage data 262 to the power source 112. At 607, the method determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118. If the output electrodes 134a and/or 134b are not activated, the method loops until the output electrodes 134a and/or 134b are activated. Otherwise, at 609, the method sets a counter to a value equal to zero.

At 608, the method determines, based on the activation data 264, whether one or more of the output electrodes 134a-134j have been activated such that the voltage applied to the respective input electrode 132a-132j has caused current to pass through the fluid 118 in the internal channel 152 to the respective output electrode 134a-134j. If one or more of the output electrodes 134a-134j are not activated, the method loops until one or more of the output electrodes 134a-134j are activated.

If one or more of the output electrodes 134a-134j are determined to be activated, based on the receipt of activation data 264, at 610, the method determines which of the output electrodes 134a-134j is activated by the fluid 118 flowing within the internal channel 152 (FIG. 2). At 612, the method determines, based on the current increment of the counter, which pre-defined volume of fluid was received into the test housing 130 based on the test fluid quantity data 230 received as input data 210. At 614, the method associates the identified pre-defined volume of fluid received into the test housing 130 with the respective one or more of the activated output electrode 134a-134j for the particular test housing 130 identified in the test device data 226, and stores this data as test device calibration data 268 in the calibration datastore 204.

At 616, the method determines whether each of the output electrodes 134a-134j in the test housing 130 has been activated based on the activation data 264 that has been received. If true, the method proceeds to 618. Otherwise, the method proceeds to 620. At 620, the method increments the counter by one and loops to 608.

At 618, the method commands the power source 112 to cease applying the voltage to alternating ones of the input electrodes 132a-132j of the fluid delivery test device 106 or outputs the stop voltage command 270 to the power source 112. The method ends at 622.

Figure 12:
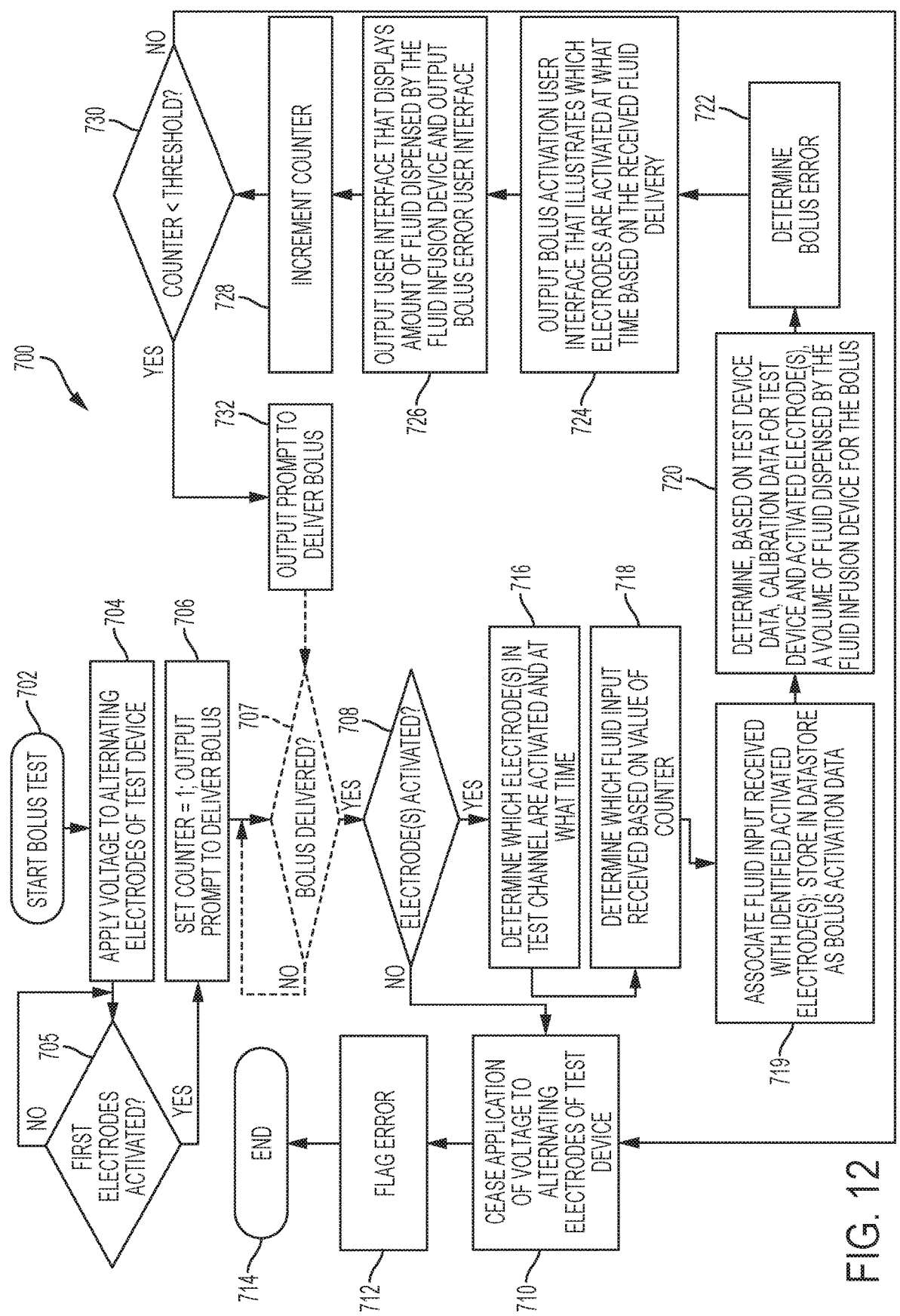
FIG. 12 is a flowchart illustrating a bolus test control method for the test system of FIG. 1, in accordance with various embodiments.

Referring now to FIG. 12, and with continued reference to FIGS. 1-5, a flowchart illustrates a bolus test method 700 that can be performed by the test control system 200 of FIGS. 1-5 in accordance with the present disclosure. In various embodiments, the bolus test method 700 is performed by the processor 180 of the controller 114. As can be appreciated in light of the disclosure, the order of operation within the method is not limited to the sequential execution as illustrated in FIG. 12, but may be performed in one or more varying orders as applicable and in accordance with the present disclosure. In various embodiments, the bolus test method 700 can be scheduled to run based on one or more predetermined events, such as based on the receipt of the input data 210. Prior to beginning the bolus test method, the operator inputs commands to a user interface of the fluid infusion device 102 to prime the fluid infusion device 102 and the test housing 130.

The method begins at 702. At 704, the method commands the power source 112 to apply a voltage to alternating ones of the input electrodes 132a-132j of the fluid delivery test device 106 or outputs the voltage data 262 to the power source 112. At 705, the method determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118. If the output electrodes 134a and/or 134b are not activated, the method loops until the output electrodes 134a and/or 134b are activated.

At 706, the method sets a counter to a value equal to zero, and optionally, outputs the prompt user interface 257 to instruct the user to dispense the bolus. At 707, optionally, the method determines, based on the bolus delivery data 217, whether the bolus has been delivered. If true, the method proceeds to 708. Otherwise, if false, the method loops.

At 708, the method determines, based on the activation data 264, whether one or more of the output electrodes 134a-134j have been activated such that the voltage applied to the respective input electrode 132a-132j has caused current to pass through the fluid 118 in the internal channel 152 to the respective output electrode 134a-134j. If one or more of the output electrodes 134a-134j are not activated, the method proceeds to 710. At 710, the method commands the power source 112 to cease applying the voltage to alternating ones of the input electrodes 132a-132j of the fluid delivery test device 106 or outputs the stop voltage command 270 to the power source 112. The method flags an error at 712. The method ends at 714.

Otherwise, if one or more of the output electrodes 134a-134j are determined to be activated, based on the receipt of activation data 264, at 716, the method determines which of the output electrodes 134a-134j is activated by the fluid 118 flowing within the internal channel 152 (FIG. 2) and at what time based on time data 266 received from other modules associated with the controller 114. At 718, the method determines, based on the current increment of the counter, which volume of fluid was received into the test housing 130 based on the test fluid quantity data 230 received as input data 210. At 719, the method associates the identified volume of fluid received into the test housing 130 with the respective one or more of the activated output electrodes 134a-134j at the current time for the particular test housing 130 identified in the test device data 226, and stores this data as bolus activation data 248 in the bolus datastore 404.

At 720, the method determines a volume of fluid delivered by the fluid infusion device 102 based on equation (2), the calibration data 258, the test device data 226 and the output electrodes 134a-134j that were activated. At 722, the method determines the bolus error data 236. At 724, the method outputs the bolus activation user interface 250 that illustrates when the output electrodes 134a-134j were activated at a particular time based on the received fluid or bolus delivered by the fluid infusion device 102. At 726, the method outputs the bolus amount user interface 234 that illustrates the volume of fluid or bolus delivered by the fluid infusion device 102 for the particular count of the counter and outputs the bolus error user interface 238 that illustrates the error associated with each volume of fluid or bolus delivered by the fluid infusion device 102 for the particular count of the counter.

At 728, the method increments the counter by one. At 730, the method determines whether the counter is less than the pre-defined threshold count. If the counter is less than the pre-defined threshold count, at 732, the method outputs the prompt user interface 257 and proceeds to 707. Otherwise, if the counter is greater than the pre-defined threshold count, the method proceeds to 710.

Figure 13:
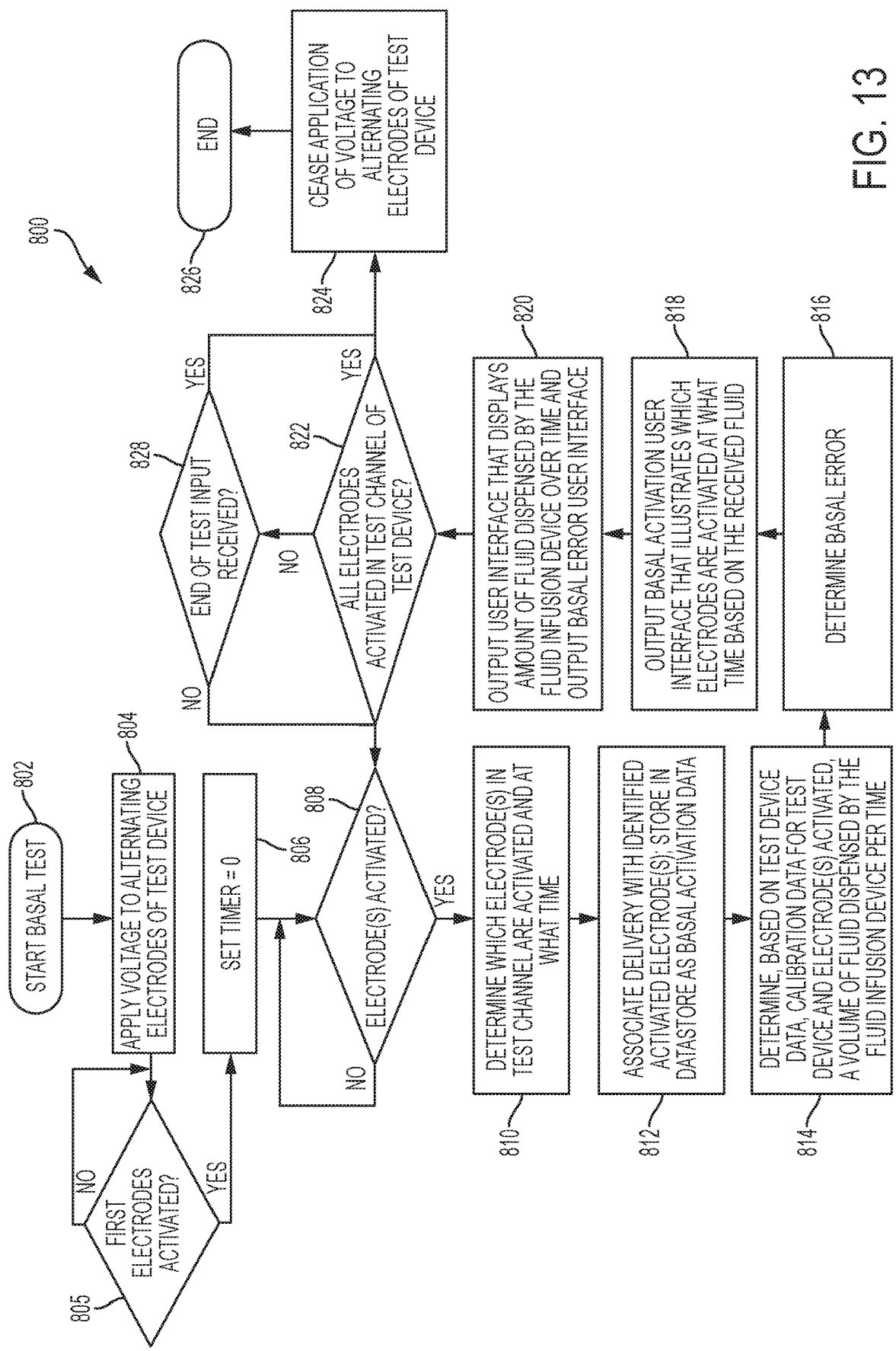
FIG. 13 is a flowchart illustrating a basal test control method for the test system of FIG. 1, in accordance with various embodiments.

Referring now to FIG. 13, and with continued reference to FIGS. 1-5, a flowchart illustrates a basal test method 800 that can be performed by the test control system 200 of FIGS. 1-5 in accordance with the present disclosure. In various embodiments, the basal test method 800 is performed by the processor 180 of the controller 114. As can be appreciated in light of the disclosure, the order of operation within the method is not limited to the sequential execution as illustrated in FIG. 13, but may be performed in one or more varying orders as applicable and in accordance with the present disclosure. In various embodiments, the basal test method 800 can be scheduled to run based on one or more predetermined events, such as based on the receipt of the input data 210. Prior to beginning the basal test method, the operator inputs commands to a user interface of the fluid infusion device 102 to prime the fluid infusion device 102 and the test housing 130.

The method begins at 802. At 804, the method commands the power source 112 to apply a voltage to alternating ones of the input electrodes 132a-132j of the fluid delivery test device 106 or outputs the voltage data 262 to the power source 112. At 805, the method determines, based on the activation data 264, whether the output electrode 134a and/or the output electrode 134b has been activated such that the voltage applied to the input electrode 132a has caused current to pass through the fluid 118 in the internal channel 152 to the respective output electrode 134a and/or 134b, which indicates that the test housing 130 has been primed with the fluid 118. If the output electrodes 134a and/or 134b are not activated, the method loops until the output electrodes 134a and/or 134b are activated.

At 806, the method sets a timer to a value equal to zero. At 808, the method determines, based on the activation data 264, whether one or more of the output electrodes 134a-134j have been activated such that the voltage applied to the respective input electrode 132a-132j has caused current to pass through the fluid 118 in the internal channel 152 to the respective output electrode 134a-134j. If one or more of the output electrodes 134a-134j are not activated, the method loops.

Otherwise, if one or more of the output electrodes 134a-134j are determined to be activated, based on the receipt of activation data 264, at 810, the method determines which of the output electrodes 134a-134j is activated by the fluid 118 flowing within the internal channel 152 (FIG. 2) and at what time based on time data 266 received from other modules associated with the controller 114. At 812, the method associates the volume of fluid received into the test housing 130 with the respective one or more of the activated output electrodes 134a-134j at the current time of the timer, and stores this data as basal activation data 252 in the basal datastore 408.

At 814, the method determines a volume of fluid delivered by the fluid infusion device 102 per time based on equation (3), the calibration data 258, the test device data 226, the value of the timer and the output electrodes 134a-134j that were activated. At 816, the method determines the basal error data 244 using equation (4). At 818, the method outputs the basal activation user interface 254 that illustrates when the output electrodes 134a-134j were activated at a particular time based on the fluid delivered by the fluid infusion device 102. At 820, the method outputs the basal rate user interface 242 that illustrates the volume of fluid or bolus delivered by the fluid infusion device 102 over the time measured by the timer and outputs the basal error user interface 246 that illustrates the error associated with the amount of fluid received from the fluid infusion device 102 over the time measured by the timer.

At 822, the method determines whether each of the output electrodes 134a-134j in the test housing 130 has been activated based on the activation data 264 that has been received. If true, the method proceeds to 824. At 824, the method commands the power source 112 to cease applying the voltage to alternating ones of the input electrodes 132a-132j of the fluid delivery test device 106 or outputs the stop voltage command 270 to the power source 112. The method ends at 826.

Otherwise, if each of the output electrodes 134a-134j have not been activated, the method proceeds to 828. At 828, the method determines whether the end test data 219 has been received in the input data 210. If true, the method proceeds to 824. Otherwise, the method loops to 808.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A test system for measuring a volume of fluid dispensed by a fluid infusion device, comprising:
   a test housing that includes an inlet and an internal channel, the inlet to be coupled to the fluid infusion device to receive the volume of fluid, and the internal channel in fluid communication with the inlet;

an input electrode coupled to the internal channel to be in fluid communication with the volume of fluid;
an output electrode coupled to the internal channel to be in fluid communication with the volume of fluid, the output electrode coupled to the internal channel so as to be spaced apart from the input electrode;
a power source configured to create a voltage potential between the input electrode and the output electrode; and
a controller configured to:
determine whether the input electrode and the output electrode have been activated based on the voltage potential created between the input electrode and the output electrode causing the volume of fluid in the internal channel to conduct current between the input electrode and the output electrode; and
determine a measurement of the volume of fluid dispensed by the fluid infusion device based on whether the input electrode and the output electrode have been activated.

2. The test system of claim 1, wherein the input electrode comprises a plurality of input electrodes and the output electrode comprises a plurality of output electrodes, and each of the plurality of input electrodes is coupled to the internal channel so as to be associated with the plurality of output electrodes.

3. The test system of claim 2, wherein the power source is configured to apply the voltage to each of the plurality of input electrodes in a sequential pattern.

4. The test system of claim 3,
wherein each one of the plurality of input electrodes and associated output electrode of the plurality of electrodes forms a respective graduation of a plurality of graduations; and
wherein, to determine the measurement of the volume of fluid, the controller is configured to select a graduation from the plurality of graduations based on whether each one of the plurality of input electrodes and associated output electrode of the plurality of electrodes has been activated while the power source applies the voltage to each of the plurality of input electrodes in the sequential pattern.

5. The test system of claim 1, wherein the test housing has a first housing side opposite a second housing side, the input electrode is coupled to the first housing side so as to be at least partially received within the internal channel and the output electrode is coupled to the second housing side so as to be at least partially received within the internal channel.

6. The test system of claim 5, wherein the test housing has a first housing surface that interconnects the first housing side and the second housing side, and the inlet is defined through the first housing surface.

7. The test system of claim 6, wherein the test housing has a first housing end and an opposite second housing end, the internal channel extends through the test housing from the first housing end to the second housing end and the inlet is defined through the first housing surface proximate the first housing end so as to be spaced a distance apart from the input electrode.

8. The test system of claim 1, wherein the input electrode has an end that extends into the internal channel to be in communication with the fluid.

9. The test system of claim 8, wherein the output electrode has a second end that extends into the internal channel that is spaced apart from the end of the input electrode such that a gap is defined within the internal channel between the end of the input electrode and the second end.

10. The test system of claim 1, wherein the fluid infusion device is an infusion device that is fluidly coupled to the test housing by an infusion set, with a portion of the infusion set received within the inlet and in fluid communication with the internal channel.

11. The test system of claim 1, wherein the fluid is an electrically conductive fluid.

12. A test system for measuring a volume of fluid dispensed by a fluid infusion device, comprising:
a test housing that includes an inlet and an internal channel, the inlet to be coupled to the fluid infusion device to receive the volume of fluid, and the internal channel in fluid communication with the inlet;
a plurality of input electrodes coupled to the internal channel to be in fluid communication with the volume of fluid;
a plurality of output electrodes coupled to the internal channel to be in fluid communication with the volume of fluid, the plurality of output electrodes spaced apart from a respective one of the plurality of input electrodes;
a power source configured to apply, to at least one of the plurality of input electrodes, a voltage to the respective one of the plurality of input electrodes; and
a controller configured to:
determine whether the respective one of the plurality of input electrodes and the respective at least one of the plurality of output electrodes have been activated based on the voltage potential created between the respective one of the plurality of input electrodes and the respective at least one of the plurality of output electrodes causing the volume of fluid in the internal channel to conduct current between the respective one of the plurality of input electrodes and the respective at least one of the plurality of output electrodes; and
determine a measurement of the volume of fluid dispensed by the fluid infusion device based on whether the respective one of the plurality of input electrodes and the respective at least one of the plurality of output electrodes have been activated.

13. The test system of claim 12, wherein the power source is configured to apply the voltage to each of the plurality of input electrodes in a pattern.

14. The test system of claim 12, wherein the power source is configured to apply the voltage to each of the plurality of input electrodes in a sequential pattern.

15. The test system of claim 12, wherein the test housing has a first housing side opposite a second housing side, the plurality of input electrodes is coupled to the first housing side so as to be at least partially received within the internal channel and the plurality of output electrodes is coupled to the second housing side so as to be at least partially received within the internal channel.

16. The test system of claim 15, wherein the test housing has a first housing end and an opposite second housing end and a first housing surface that interconnects the first housing end and the second housing end, the internal channel extends through the test housing from the first housing end to the second housing end and the inlet is defined through the first housing surface proximate the first housing end so as to be spaced a distance apart from a first one of the plurality of input electrodes.

17. The test system of claim 16, wherein the fluid infusion device is an insulin infusion device that is fluidly coupled to the test housing by an infusion set, the infusion set to be coupled to the first housing surface such that a portion of the infusion set is received within the inlet to be in fluid communication with the internal channel.

18. The test system of claim 12, wherein the fluid is an electrolytic solution.

19. The test system of claim 12, wherein each of the plurality of input electrodes has an end that extends into the internal channel to be in communication with the fluid, each of the plurality of output electrodes has a second end that extends into the internal channel that is spaced apart from the end of the respective one of the plurality of input electrodes such that a gap is defined within the internal channel between the end of the respective one of the plurality of input electrodes and the second end of the respective one of the plurality of output electrodes.

20. A test system for measuring a volume of fluid dispensed by a fluid infusion device, comprising:
- a test housing that includes an inlet and an internal channel, the inlet to be coupled to the fluid infusion device to receive the volume of fluid, and the internal channel in fluid communication with the inlet;
- a plurality of input electrodes coupled to the internal channel to be in fluid communication with the volume of fluid;
- a plurality of output electrodes coupled to the internal channel to be in fluid communication with the volume of fluid, each one of the plurality of output electrodes spaced apart from a respective one of the plurality of input electrodes;
- a power source configured to apply, to at least one of the plurality of input electrodes, a voltage to the respective one of the plurality of input electrodes,
- wherein each of the plurality of input electrodes has an end that extends into the internal channel to be in communication with the fluid, each of the plurality of output electrodes has a second end that extends into the internal channel that is spaced apart from the end of the respective one of the plurality of input electrodes such that a gap is defined within the internal channel between the end of the respective one of the plurality of input electrodes and the second end of the respective one of the plurality of output electrodes; and
- a controller configured to:
  - determine whether the end of the respective one of the plurality of input electrodes and the second end of the respective one of the plurality of output electrodes have been activated based on the voltage potential created between the end of the respective one of the plurality of input electrodes and the second end of the respective one of the plurality of output electrodes causing the volume of fluid in the internal channel to conduct current between the end of the respective one of the plurality of input electrodes and the second end of the respective one of the plurality of output electrodes; and
  - determine a measurement of the volume of fluid dispensed by the fluid infusion device based on whether the end of the respective one of the plurality of input electrodes and the second end of the respective one of the plurality of output electrodes have been activated.

* * * * *